(12) United States Patent
Deo

(10) Patent No.: US 12,178,677 B2
(45) Date of Patent: Dec. 31, 2024

(54) THERMALLY DISRUPTING BIOFILM, DISINFECTING, OR SEALING TOOTH

(71) Applicant: Anand Deo, Mendota Heights, MN (US)

(72) Inventor: Anand Deo, Mendota Heights, MN (US)

( * ) Notice: Subject to any disclaimer, the term of this patent is extended or adjusted under 35 U.S.C. 154(b) by 0 days.

(21) Appl. No.: 18/462,078

(22) Filed: Sep. 6, 2023

(65) Prior Publication Data

US 2024/0074832 A1    Mar. 7, 2024

Related U.S. Application Data

(60) Provisional application No. 63/516,379, filed on Jul. 28, 2023, provisional application No. 63/374,699, filed on Sep. 6, 2022.

(51) Int. Cl.
  *A61C 5/55*    (2017.01)

(52) U.S. Cl.
  CPC ...................... *A61C 5/55* (2017.02)

(58) Field of Classification Search
  CPC ......... A61C 5/55; A61C 19/06; A61B 5/1491; H05B 6/46; H05B 6/00; H05B 6/50; A61F 7/12; A61F 7/007; H10N 30/00; H01L 21/67103
  See application file for complete search history.

(56) References Cited

U.S. PATENT DOCUMENTS

| | | |
|---|---|---|
| 7,125,254 B2 | 10/2006 | Calvert |
| 7,470,124 B2 | 12/2008 | Bornstein |
| 10,553,462 B2 * | 2/2020 | Deo .................. H05B 6/50 |
| 12,004,994 B1 * | 6/2024 | King .................. A61F 7/0085 |
| 2002/0135103 A1 * | 9/2002 | Odorzynski ........ A61F 13/4902 264/479 |
| 2004/0009452 A1 * | 1/2004 | Oh .................. A61C 5/62 433/81 |
| 2013/0122450 A1 * | 5/2013 | Simons .................. A61C 5/55 433/32 |
| 2014/0087333 A1 | 3/2014 | Divito et al. |

(Continued)

OTHER PUBLICATIONS

"International Application Serial No. PCT/US2023/073556, International Search Report mailed Dec. 4, 23", 4 pgs.

(Continued)

*Primary Examiner* — Yogesh P Patel
(74) *Attorney, Agent, or Firm* — Schwegman Lundberg & Woessner, P.A.

(57) ABSTRACT

Drilling an infected tooth root canal can leave some infected material behind. Heat delivered from within the tooth can be used to disrupt biofilm, disinfect, and/or seal. A cone-shaped flexible device can be inserted into or toward the root canal. The device can include a heating transducer, such as a DC resistive heating element, or an RF heating transducer that can generate heat in a dielectric or semiconductor or polymer active substrate, with a locus of the heat generation controllable by adjusting a frequency of an electrical input signal driving the heating transducer. Thermally conductive fluid can be introduced into the root canal to help distribute heat from the heating transducer to nearby portions of the root canal for heat disinfecting treatment of infected tissue. The active substrate can be heat-softenable, such as to help seal a target region of the tooth.

12 Claims, 18 Drawing Sheets

(56) References Cited

U.S. PATENT DOCUMENTS

2014/0220511 A1    8/2014  DiVito et al.
2017/0281312 A1*  10/2017  Khakpour ............ A61C 17/024
2020/0176283 A1*   6/2020  Deo ................. H01L 21/67103
2022/0108899 A1    4/2022  Deo

OTHER PUBLICATIONS

"International Application Serial No. PCT/US2023/073556, Written Opinion mailed Dec. 4, 23", 8 pgs.

* cited by examiner

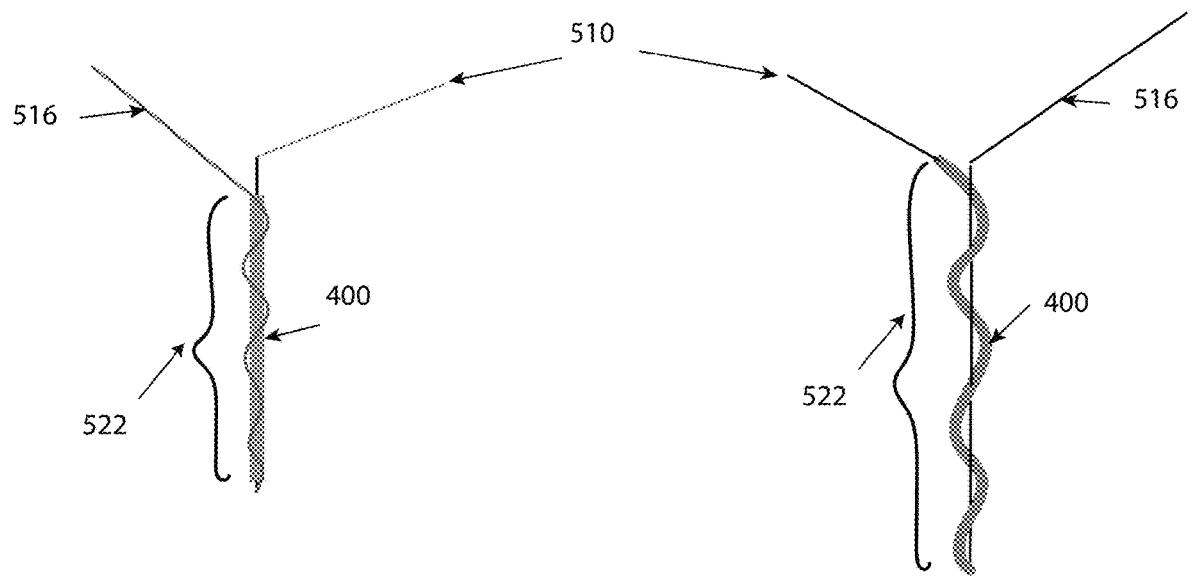

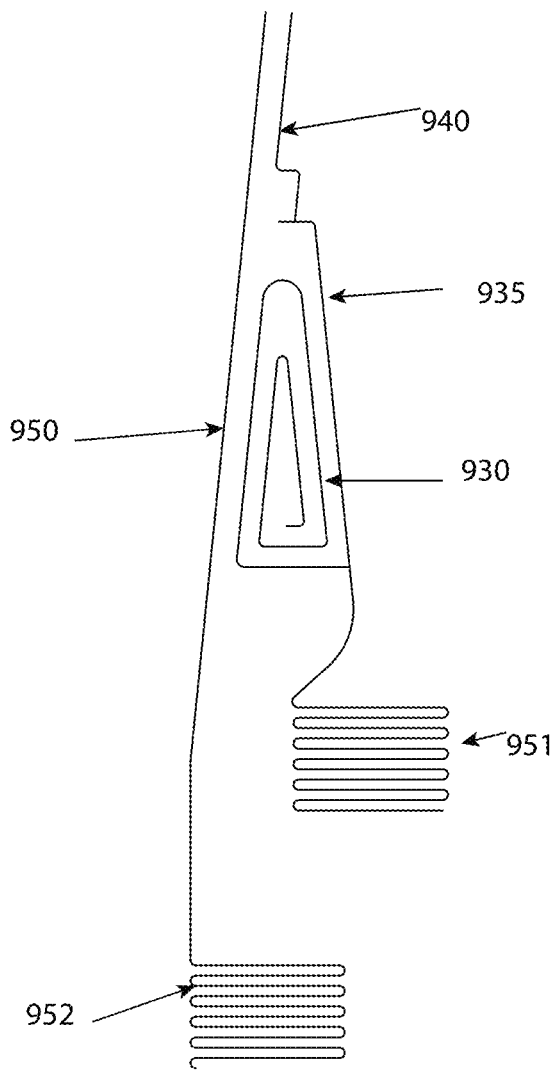

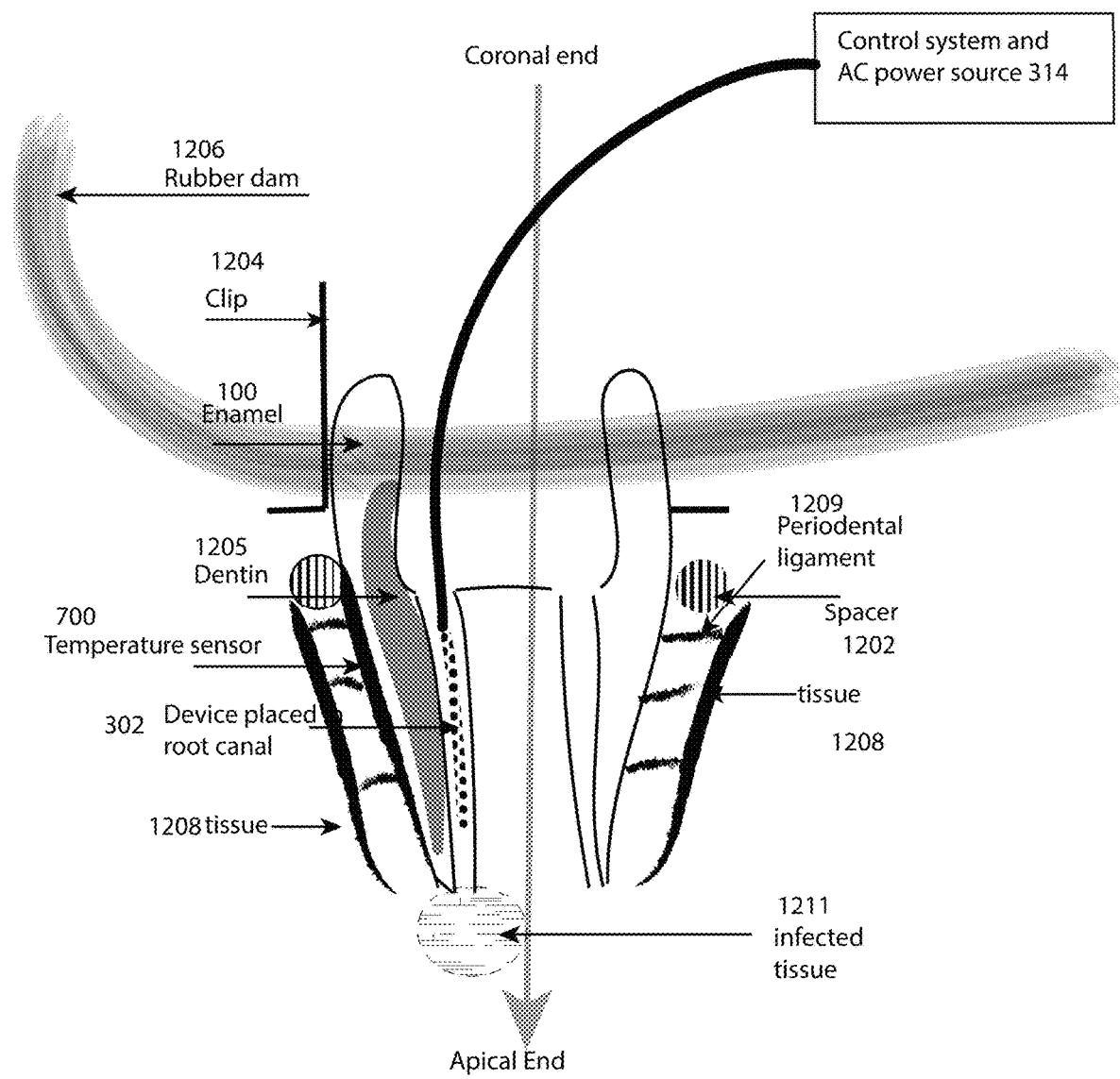
Figure 12 Sample treatment setup cross-section

THERMALLY DISRUPTING BIOFILM, DISINFECTING, OR SEALING TOOTH

CLAIM OF PRIORITY

This patent application claims the benefit of priority of each of: (1) Anand Deo U.S. Provisional Patent Application No. 63/374,699, filed Sep. 6, 2022 entitled "THERMAL DISINFECTION AND DENTAL ROOT CANAL TREATMENT,"; and (2) Anand Deo U.S. Provisional Patent Application No. 63/516,379, filed Jul. 28, 2023 entitled "THERMAL DENTAL TREATMENT TO DISRUPT BIOFILM OR TO DISINFECT OR SEAL A TOOTH,"; the benefit of priority of each of which is claimed, and each of which is incorporated by reference herein in its entirety.

TECHNICAL FIELD

This document pertains generally, but not by way of limitation, to dental treatment, and more particularly, but not by way of limitation to thermal dental treatment to disrupt biofilm, to disinfect a tooth, to seal a tooth, or any combination of these, such as during a root canal or other dental procedure.

BACKGROUND

Infection can occur when the seal of a natural human or other biological body structure is broken, or when a foreign substance or body enters or is placed inside the human body. Teeth are an example of such a naturally-sealed structure.

For example, dental infections inside the tooth can be caused by a cavity within the tooth being exposed to and retaining bacteria that can infect the tooth. In a healthy tooth, the only anatomical opening exists at the apical end of the tooth into the root canal of the tooth. Therefore, if the base of a tooth gets infected, the infection can make its way into the root canal of the tooth. The forces experienced by teeth are significant under day-to-day usage. These forces may cause cracks. Cracks in the tooth structure can further lead to cavities and dental infections.

Current treatment for infected root canals involves drilling deep into the root canal. In addition to drilling, the root canal treatment procedure can also involve grinding, filing, or both. Any of drilling, grinding, or filing will remove tooth material. Drilling also creates microparticles or burr. Drilling also pushes a mixture of organic material and burr into the surrounding dentin. Bacteria can get trapped in the mixture. Therefore, bacteria can get compacted inside the dentin via the root canal drilling. This can result in continued infection that can fester or linger even after treating an infected root canal by drilling.

SUMMARY

The present inventor has recognized, among other things, that a bolus of heat (e.g., continuous, or pulsed) can be used to help disinfect or sterilize or seal a desired location within the body, such as within a tooth. This document describes, among other things, devices and methods that can help reduce, minimize, or even eliminate the need to drill deep into the root canals, although the present techniques can also be usable and useful in combination with drilling. The present techniques can include enabling placing a heat-creating device inside the tooth at a target location to be treated, such as within a root canal cavity of the tooth. The heat that can be introduced from the interior of the tooth can be used to help disintegrate biofilm, disinfect, or seal the infected region or other target region to be treated, or can be used for any combination of these.

The present techniques can help treat the existing infection in the tooth root, such as by killing the infectious bacteria in the tooth system, and disrupting, degenerating, or inhibiting biofilm such as by using localized applied heat, such as can be applied from within the tooth. The tooth system can be considered to include not only the tooth and the tooth root, but can also include the dentin and can include tissue at the base of the apical end of the tooth. The present techniques can also include optionally sealing a desired portion of a tooth. This sealing can optionally be carried out concurrently with the applying heat for disinfection or for biofilm disruption.

On a case-by-case basis it is also possible to disinfect or otherwise treat several tooth root systems at once. In a tooth with multiple roots, the decision as to whether to treat multiple roots concurrently (e.g., multiple roots within the same tooth, or in different teeth) may depend on availability of space and the ability of the tooth structure to withstand the thermal energy of multiple devices operating concurrently. Beyond the time savings in treating multiple tooth roots concurrently, such an approach may help provide a more complete disinfection of the tooth. That is because tooth root systems are interconnected in the pulp chamber, such that it is quite possible that infection has spread to a neighboring root, e.g., in the same tooth or in an adjacent tooth.

Although this document focuses on the specific use case in which the targeted treatment region includes a root canal or other tooth cavity of the tooth, the present techniques can also be applied to other target regions of the tooth or elsewhere within a human or other biological body.

Several different factors can be major contributors to root canal treatment failures. First, tooth structure can be reduced due to cleaning or drilling. This can be a major contributor for later tooth fractures. Such tooth fractures can create open spaces that can permit bacterial entry and infection. Second, coronal (top-down) bacterial leakage can occur. This can cause recurrent infections. Third, there can be apical backflow (bottom-up) dispersion of infected fluid into the tooth root system. This can occur during a time period between disinfecting or otherwise treating a targeted treatment region and then later sealing the target treatment region.

For example, the basal tissue at the base of the root canal of the tooth may become infected. Infected basal tissue may also be disinfected, cauterized, or otherwise treated, such as by using the present techniques involving localized applied heat. This can help prevent or reduce the amount of back pressure produced as part of the healing process after completing a root canal treatment. Back pressure can push infection back into the tooth root and is undesirable because it can re-infect the tooth root.

This document describes, among other things, a heat producing device that can be sized and shaped and otherwise configured for one or more of tooth root canal disinfection (or other similar in vivo or other heat disinfection application use-cases), biofilm disruption, or optional sealing by locally-applied heat, and methods of delivering disinfection, biofilm disruption, or sterilization treatment using such a heat producing device. As explained herein, the present devices and methods can deliver heat by transferring or creating sterilization-grade thermal energy. Such heat can be provided directly to a treatment location or through another medium into the tooth or other treatment location to be treated. Enough heat can be injected into an interior of the tooth system to reach infection control grade temperatures.

Moreover, this can be accomplished while maintaining an exterior of the tooth at a safe temperature such that the tooth and nearby tissue are not degraded by the bolus of heat that is delivered to the tooth.

When heat is first created in or applied to the dentin or other appropriate target region of a tooth, a transient thermal cell can be established in it. This can be thought of as a thermal battery. Thermal energy can be accumulated in the dentin of the tooth. A thermal gradient can be formed. For example, heat can be applied from the interior of the tooth and thermally conducted radially outward, starting from a portion of a heating device that has been introduced or placed into the tooth at or near the targeted treatment region of the tooth. For a defined short heat application time duration (e.g., between 5 seconds and 1.5 minutes) during which the bolus of heat is applied, temperatures toward the interior of the tooth can be hotter than temperatures toward the exterior of the tooth or hotter than temperatures outside and adjacent to the tooth. Therefore, temperatures inside the thermal cell that can be established within the tooth, during the short heat application time duration, can be as high as, for example, 78° C. Applying such a temperature for a short heat application time duration can be effective to kill *Streptococcus aureus* bacteria in the interior targeted treatment region of the tooth. Meanwhile, temperature outside of the tooth enamel or tooth cementum can be maintained safely within a lower temperature range, such as within a safety temperature range that is elevated beyond body temperature but that does not exceed a safety temperature value that is in a range between 45° Celsius to 55° Celsius, such that the amount and duration of the heat does not cause bone or tissue necrosis. The particular safety temperature range may be determined by the particular application. Thus, while a safety temperature of up to 55 degrees Celsius can be effective at the outside of the tooth cementum of the root canal being disinfected, a different safety temperature may be suitable for another application.

To recap, transient thermal energy can be stored in (and optionally confined to) a region such as to establish a thermal gradient in or near the region for a certain duration. A transient thermal cell may be understood as a region in which a temporal gradient in heat storage and (corresponding temperature gradients) are formed until a thermal equilibrium occurs. The exact duration of the temperature gradient before thermal equilibrium temperatures are reached may be case specific.

As explained herein, the present techniques can also include optionally sealing a desired portion of a tooth. This can optionally be carried out concurrently with applying heat for disinfection or biofilm disruption. As described herein, the heating device can include a conformal active (e.g., lossy dielectric) polymer substrate. The conformal active polymer substrate can be thin enough to be rolled, folded, or otherwise shaped, such as into a cone or a cylinder or a similar elongate configuration. The conformal active polymer substrate can be flexible and conformal and resilient enough such that when it is then introduced into a tooth cavity such as a tooth root canal, it can assume a cone-like shape (or other shape that conforms with the internal wall surface of the root canal or tooth cavity) when inserted into a tooth cavity or the tooth root canal. The polymer substrate can conform to the shape and space available within the tooth cavity or the tooth root canal. Heat can be generated in the conformal active polymer substrate by applying an AC electromagnetic input signal to electrically conductive input terminals that can be printed on or otherwise formed on the conformal active polymer substrate. The electrically conductive input terminals can be operatively associated with electrically conductive traces on the conformal active polymer substrate. These electrically conductive traces on the conformal active polymer substrate can form one or more resonators or other structures by which a heating or other transducer can be addressed, actuated, or both. Such resonators can be printed on or otherwise formed on the active polymer substrate, such as in a similar manner as the input terminals. A locus of heat generation in the active polymer substrate can be selectively established or addressed or optionally adjustably controlled, such as by specifying or adjusting an AC frequency of the applied electrical input signal. Providing AC frequency selection of the locus of the heat generation can be a space-efficient way of providing such heating locus selection. However, if space permits, a multiplexer, decoder, or an arrangement of one or more switches can be additionally or alternatively employed to select such heating locus. Once the heating device is placed into the root canal or other dental target treatment site, then heating treatment can be initiated. The heat generated in the interior region of the tooth can create a localized disinfection grade temperature inside the root canal. Optionally, the conformal active polymer substrate of the heating device can be made of biocompatible materials that can be selected to heat-soften in response to the disinfection heat, as described herein, such as to enable concurrently sealing a target region of a tooth in addition to one or more of disrupting biofilm or disinfecting the target region of the tooth. Such sealing is different than an approach using warm vertical compaction of a material such as gutta percha, which involves compaction of the gutta percha material (for sealing only, but not for disinfection) using a separate heated plunger. In contrast to such an approach of using a separate heated instrument, here, the same disinfection heat produced by the heating device in the conformal polymer active substrate can cause the material of at least a portion of the heating device itself to heat-soften and conform, such that the heat-softened conformal polymer active substrate adheres and anchors to the interior of the root canal cavity or other target region of the tooth, thereby enabling concurrently sealing the targeted treatment region of the tooth together with the disinfection to help inhibit or prevent additional bacteria from entering the disinfected region. This can help avoid possibly re-introducing bacteria in an approach that would otherwise involve a separate step of sealing performed after the disinfection. In an example of the present concurrent sealing approach, the heating device can be disconnected from the control and power circuitry and left in place within the tooth to provide the seal. Alternatively, the heating device can use materials that can be specified to withstand the disinfection heat temperature generated inside the tooth, such as without softening enough to anchor the heating device to the tooth. In that case, the heating device can optionally be removed from the tooth after the heat disinfection of the target treatment region is performed. The clinician can optionally apply a heat-curable and bio-compatible adhesive to the outside surface of a distal portion of the heating device to be inserted into the tooth. The outside of the heating device comes directly in contact with the inside of root canal or other tooth cavity into which the distal portion of the heating device is inserted. In the present approach of allowing the heating device to soften to anchor a seal, the seal provided by an anchored device may also later be removed, such as for retreatment, such as by adding a solvent such as chloroform or providing some additional heat to re-soften and remove the seal from the root canal or other tooth cavity.

A heating device that is configured to anchor to the tooth, such as to provide a seal, can include a thin-film substrate heating device or a thick-film substrate heating device. Either type of substrate can carry an electrically conductive input structure, which can include electrical traces or terminals to receive electrical power. Either type of substrate can include an apron, which can be sized and shaped or otherwise particularly configured for a particular device based on its active region, thermal requirements, electrical trace geometries, and electrical power input. The apron can also serve as a cutting edge along which an individual device can be cut out from a larger sheet of the film material being used for the substrate, such as after the electrically conductive input structure and any other electrical conductors are formed or placed on the substrate. Electrical power can be input from one end of the electrical input structure. The input electrical power can provide electrical energy that can dissipate into the active substrate, such as for being transduced into heat. Relatively more electrical power exists at the input location at which the electrical power is applied. An apron can be configured to provide support for such variations in electrical power, variations in transducing the electrical power into heat, or both. For an open or linear configuration in which an edge of the substrate promotes sealing, the apron can help ensure a complete seal. Including an apron on the substrate on the distal working portion of the heating device can help provide one or more of structural, thermal, or electromagnetic stability to the device.

The present techniques of dental heat treatment can help provide certain potential advantages. First, heat can permeate regions within the tooth without the need for providing a physical path or opening all the way to the target region. Therefore, when the present heating techniques are applied, they can help reduce the extent of or need for drilling and removing portions of the tooth structure during preparation or other aspects of dental treatment. Any trapped infection can get treated without requiring drilling or otherwise forming a direct physically-opened path to the locus of the trapped infection, which would further reduce the amount of tooth structure. Reducing the amount of tooth structure removed during a treatment procedure can, in turn, help decrease the possibility of further fractures or cavities being formed in the tooth. The heat can treat the intact dentin, without requiring perforating or forming a physical opening into the dentin. Thus, any bacteria that have been spread into the dentin, such as during previous drilling, grinding, filing, or the like, can be heat-sterilized to help prevent recurrence of infection after the procedure is complete.

In certain cases in which the clinical need to seal is less, but in which the clinical need to reach more deeply into crevasses of the dentin is more important, the clinician may optionally place a fluid such as glycerin into the root canal or other tooth cavity before treating it. Glycerin is sticky and is an excellent thermal conductor. When heated, the gaps in the dentin may tend to open. Glycerin, when heated, becomes less viscous and can therefore spread into otherwise unreachable areas quickly, which can help enable faster spreading of heat, if desired. Even when glycerin or a fluid is optionally used, however, the dominant source of heat is thermal conduction from the heating device to the adjacent or nearby dental structures.

Second, the heating device may optionally be left within the root of the tooth after the disinfection, such as to create a seal. By allowing the optional ability to both heat-disinfect and heat-seal concurrently, the present techniques can help shield from one or both of coronal leakage (top-down) or apical backflow (bottom-up) of bacteria back into the root system.

Third, disintegrating biofilm via heat can be helpful in the treatment procedure. Heat can help disintegrate a biofilm. A biofilm disintegration temperature at the targeted treatment region within the tooth can be reached even before the disinfection temperature is reached. Therefore, biofilm disintegration can be carried out during the disinfection step before, during, and after the target treatment region reaches the temperature at which disinfection occurs. Biofilm disintegration can be an important treatment goal on its own, that is, even aside from disinfection. Accordingly, biofilm disintegration may optionally be employed without employing heat disinfection of the targeted region of the tooth, if desired. For example, biofilm disintegration can be particularly helpful in cases in which the patient's disease and tooth geometries or characteristics, such as in the presence or extent of a metallic filling in the tooth, which may not otherwise permit complete disinfection. In such cases, it can still be possible to heat-disintegrate biofilm to help flush out infection using one or more other tooth treatment processes.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 5D, 5E show two illustrative examples in which a distal portion of the heating device can include a Y-shape.

FIGS. 9C, 9D, 9E, 9F, 9G, and 9H show other examples and variations of heating devices.

FIG. 12 shows an example of a heating device as inserted into a root canal of a tooth and connected to an electrical control system.

DETAILED DESCRIPTION

Figure 1:
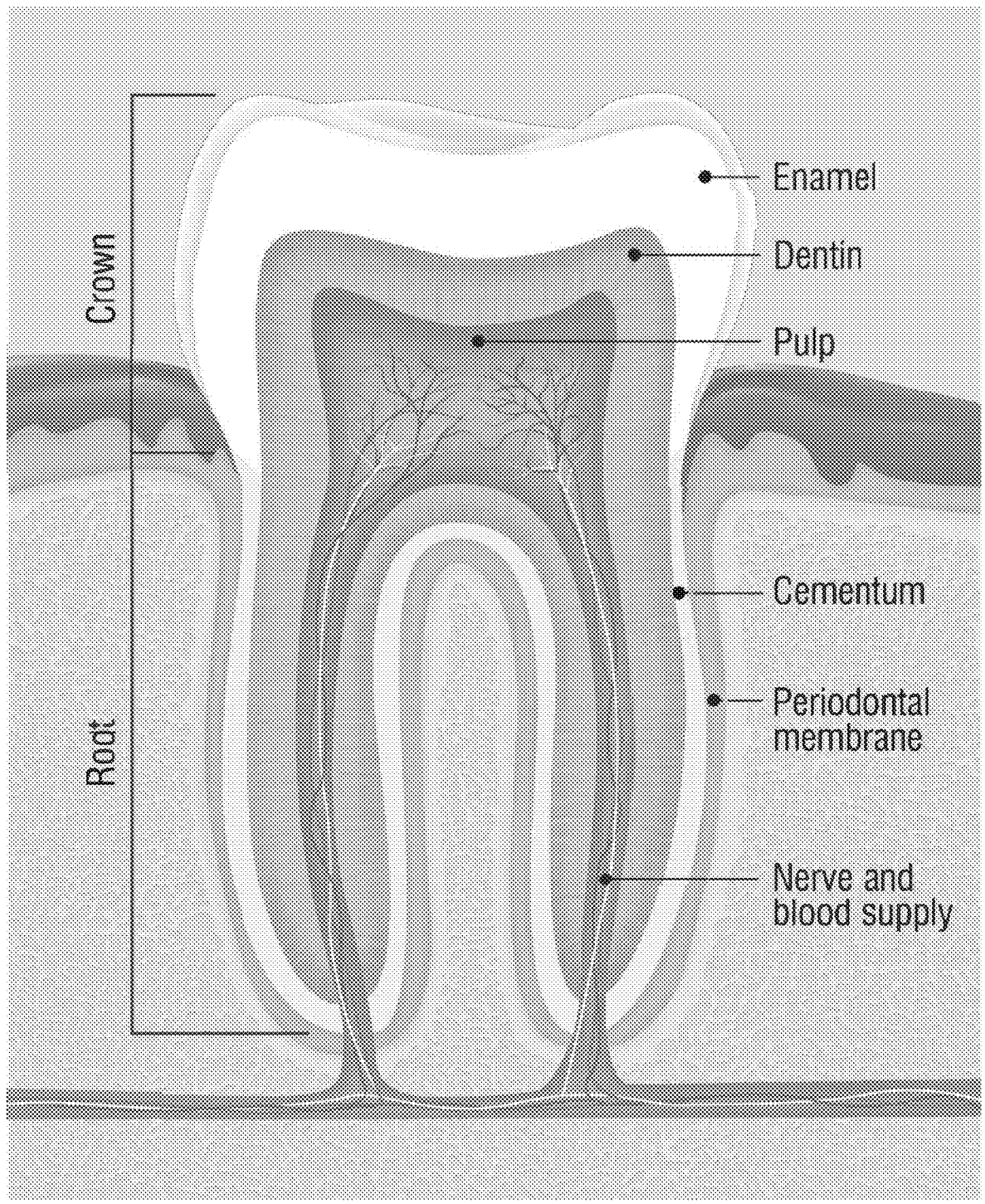
FIG. 1 is a cross-sectional picture showing an example of tooth anatomy and geometry.

This document describes, among other things, devices and methods that can be used to help disinfect a root canal or other target treatment region of a tooth—without requiring drilling deep into the tooth root canal. The present techniques can include applying localized heat to an in vivo site such as a tooth root. The applied localized heat within the tooth can help provide an improved quality of disinfection. Using the present techniques, a bolus of localized heat can be applied at the in vivo site for an appropriate short treatment duration. An efficacious sterilizing bolus of heat can be delivered in a manner such that it can reach and treat infected parts of the tooth and, if desired, as well as any infected basal tissue that is desired to be disinfected. The same or different applied localized heat can also be used to help seal a target region within the tooth.

Parts of the dental structure of the tooth can include mineral matter, organic matter, and fluid (such as water). Such a biological system can favor the present approach of applying localized heat to disinfect or sterilize or seal the tooth root or other in vivo treatment site. This is because the thermal conductivity and dielectric constant of different portions or components of the tooth can be different. For example, the thermal conductivity and the dielectric constant of the mineral portion of the tooth, which surrounds the root canal, is lower than that of water. The present techniques can use these differences within the tooth to help establish an effective transient thermal cell within the tooth.

Although not required, it may be helpful to introduce some fluid into the tooth, such as to help promote heat transfer. For example, by heating fluid that is either already present in the tooth root canal, or by supplying the in vivo treatment site via water, saline, glycerin, or another appropriate heated fluid that can be introduced from an external location and heated externally, internally, or both, the present techniques can elevate temperature at the desired in vivo treatment site. This can help ensure that all parts of the tooth root and surrounding dentin structures can be elevated quickly to an infection control grade temperature level. Moreover, this can be done without triggering a corresponding magnitude rise in temperature in the less thermally conductive mineral portion of the tooth. Thus, heat can be applied within the interior of the tooth for a duration that can allow the heat to be confined to the target treatment region in the interior of the tooth—that is, without the exterior of the tooth (and surrounding tissue, bone, ligament, or the like) being subjected to such elevated infection control grade temperature level. Instead, the surrounding tissue can be safely maintained at a lower temperature to avoid damaging or otherwise affecting the surrounding tissue by exposing such surrounding tissue, bone, or other biological structures to excess heat applied to the interior of the tooth and thermally conducted through the tooth.

Also, because heat can cause expansion of a target object exposed to such heat, applying localized heat at the in vivo target treatment site can help expand pores and possibly create new pathways for fluid flow and fluid-based localized application of heat treatment. By comparison, the tooth drilling process effectively compacts and inhibits or prevents such effective use of pores or pathways.

Patient comfort can be improved for several reasons. First, a lower tooth-gum interface temperature can be effective for providing localized heat disinfection and sterilization, making such a process comfortable for the patient. By contrast, any heat generation ancillary to drilling is not well-controlled or easily localizable. Second, deep drilling or deep filing is not required for the present techniques of applying localized heat disinfection or sterilization to the tooth root canal. More limited drilling to help provide enough access to the root canal to transfer heat into the root canal will suffice. Third, multiple root canals (of the same or different teeth) can be treated concurrently or simultaneously using the present techniques of applying localized heat. Fourth, the same step of applying localized heat for disinfection can also be used to help seal a target region within the tooth.

FIG. 1 is a cross-sectional picture showing an example of tooth anatomy and geometry. FIG. 1 shows the crown portion of the tooth, which is located above the gumline, and the root portion of the tooth, which is located below the gumline. FIG. 1 also shows enamel, dentin, pulp, nerve and blood supply passages, cementum, and periodontal membrane. The crown portion of the tooth, which is located above the gumline, includes an outer layer of tooth enamel, which does not extend below the gumline. Below the gumline, cementum is exposed as the outer layer of the tooth. A direction toward the crown portion of the tooth and away from a root portion of the tooth can be referred to as a coronal direction or a proximal direction. A direction toward the root portion of the tooth and away from the crown portion of the tooth can be referred to as an apical or distal direction.

Figure 2A:
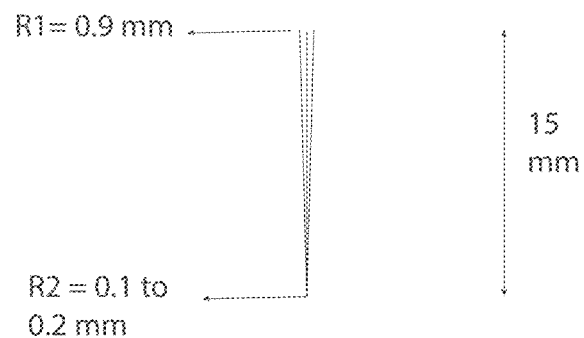
FIGS. 2A, 2B show an example of some measurements and dimensions for use of the present techniques of applying localized heat for disinfecting or sterilizing a location associated with a tooth root canal of a human tooth.
Figure 2B:
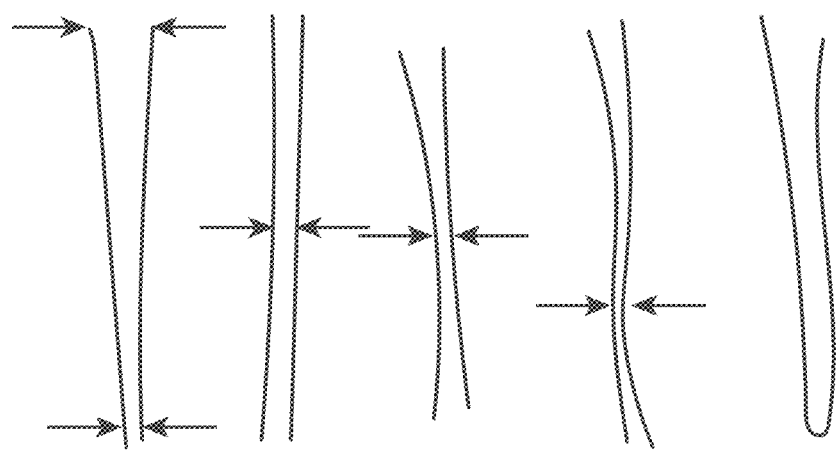

FIGS. 2A, 2B show an example of some measurements and dimensions for using the present techniques of applying localized heat for disinfecting or sterilizing a location associated with a tooth root canal of a human tooth. While measurements of root canals and internal geometries of root canals can vary, for illustrative and discussion purposes of the present techniques, the following measurements and dimensions are illustrative. For example, the average inner diameter of the tooth root at the apical end is between approximately 0.1 mm to 0.2 mm. The average outer diameter of the tooth root at the coronal end is approximately 0.9 mm. The overall approximate average length of the tooth is 15 mm. Therefore, the tooth root can be conceptualized as resembling a cone, such as shown in FIG. 2A.

FIG. 2B shows conceptually some potential variations in geometry of the tooth root canal. Some various possible tooth root canal geometries are shown in FIG. 2B to demonstrate conceptually that the root canal is not a uniform conical cavity. Its geometry can vary by person, by type of tooth, and by the disease state of the tooth, for example. The term "canal minimum opening diameter" can be used to describe the minimum access diameter along the length of the root canal. The term "linear location" of minimum diameter can be used to describe the location, along the length of the root canal from the top of the tooth towards the apical end, at which the root canal exhibits a minimal lateral dimension.

Figure 3A:
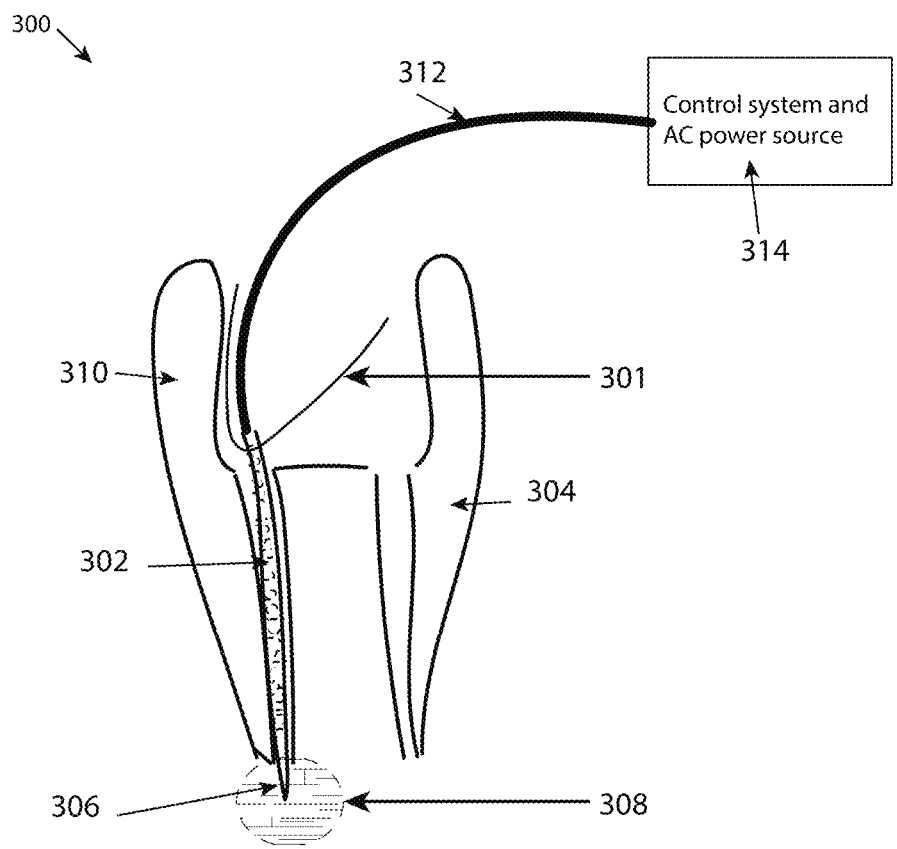
FIG. 3A shows an example of an AC powered localized heat treatment device, including a distal working portion that can be sized and shaped to fit inside a root canal of a tooth.

FIG. 3A shows an example of an AC powered localized heat treatment device 300. The heat treatment device 300 can include a cone-shaped or other elongate distal working portion 302. The distal working portion 302 can be sized and shaped to fit inside an at least partially drilled or otherwise accessed root canal or other portion of a tooth 304. Optionally, the distal working portion 302 can be sized and shaped such that a distal tip 306 of the distal working portion 302 can optionally be extended out beyond the base of the root of the tooth 304 and into the underlying nearby surrounding tissue 308. FIG. 3A also shows an example of the tooth calcium or mineral component 310 of the tooth 304. A plug or other thermal shield 301 can be located at the point of insertion into the tooth root. The thermal shield 301 can extend laterally outward, such as to help inhibit or prevent undesired heat transfer into the tooth enamel or other dental structure that are not being treated. The distal working portion 302 can provide a thin elongate insertable heating portion of the device 300 that can be connected, via a tether such as an instrumentation lead 312, to a control system and AC electrical power source 314.

Figure 3B:
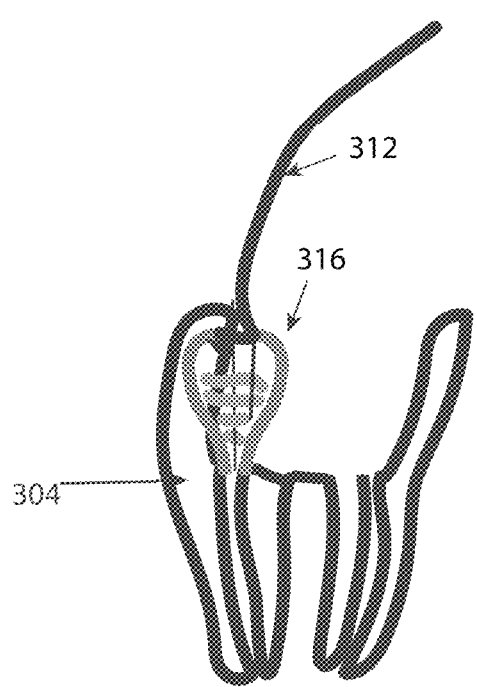
FIGS. 3B, 3C, and 3D show examples in which the system can include a fluid reservoir or a fluid conduit to supply a thermally conductive liquid for heat disinfection of the root canal.
Figure 3C:
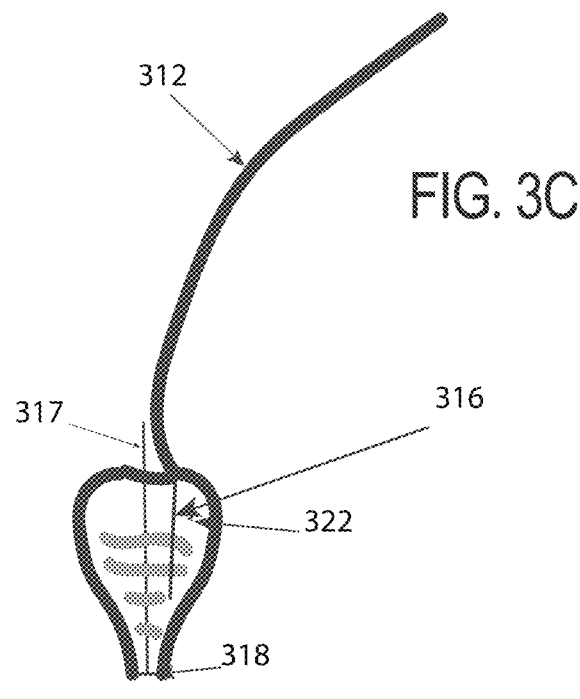
Figure 3D:
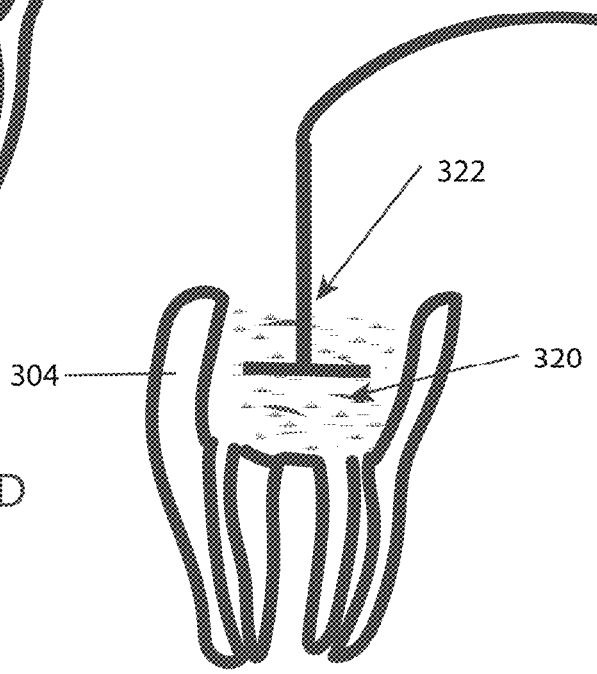

FIGS. 3B, 3C, and 3D show examples in which the device 300 can optionally include an external fluid reservoir 316, which can be different from or combined with the thermal shield 301. An optional fluid-carrying conduit 318 can extend from the fluid reservoir 316 or from the instrumentation lead 312. The fluid-carrying conduit 318 can supply a liquid into a drilled-out or other liquid-receiving recessed portion 320 of the tooth 304. The recessed portion 320 of the tooth 304 can extend at least partially into the infected root canal or other target region of the tooth 304 to be treated. Fluid from the reservoir 316 or from the instrumentation lead 312 can be delivered via the fluid-carrying conduit 318, such as for providing heat sterilization or disinfection treatment to a target region of the tooth 304. For example, the fluid can be heated in the external reservoir 316. The heated fluid can be introduced, via the fluid conduit 318 or via the instrumentation lead 312, into the tooth 304 and, in particular, into the root canal to be disinfected. Various possible examples are presented.

FIG. 3B shows an example in which the liquid or fluid reservoir 316 can be self-contained, such as in a sealed dropper or a sealed pouch or sealed pocket-like arrangement. The fluid to be heated for sterilizing the tooth 304 can be located within the reservoir 316, such as which can include a sealed dropper, pouch, pocket, or the like. The distal tip of the reservoir 316 (or a fluid conduit 318 extending therefrom) can be sized and shaped to fit into the proximal opening of the root canal. Once the fluid is heated in the reservoir 316, the distal tip of the reservoir 316 (or the fluid conduit 318 extending therefrom) can be opened, such as by one or more of puncturing (e.g., using a puncture wire 317), opening a valve, or actuating a pump that can be coupled to the reservoir 316. In response, the heated fluid can be allowed to flow from the reservoir 316 into the recessed portion 320 of the tooth 304, such as to the at least partially drilled root canal. Continuous or ongoing heating capability for heating the fluid can be provided, if desired. Such heating capability can help raise the overall temperature inside the root canal to an appropriately high temperature, such as for one or more of disrupting biofilm, disinfecting the root canal, or sealing, such as described herein.

FIG. 3C shows an example of the heated fluid reservoir 316 being separate from the tooth 304. A fluid conduit 318 can be placed between the fluid reservoir 316 and the tooth 304, such as to transport the heated fluid toward and into the tooth 304.

FIG. 3D shows an example in which a recess or cavity 320 can be created in the tooth 304, such as via access drilling or grinding or the like. The fluid reservoir 316 can be provided by or inserted into the cavity 320 in the tooth 304. Heating of the fluid can be carried out in the cavity 320, such as by a heating transducer 322 that can be located on the distal working portion 302 of the heating device 300. The heating transducer 322 can include a conformal active polymer substrate and electrical traces, such as described herein. Therefore, in the example of FIG. 3D, the fluid reservoir 316 need not be a self-contained and sealed reservoir 3316. Instead, the recess or cavity 320 can optionally serve as the fluid reservoir 316 in the tooth 304. The recess or cavity 320 can be open to the subject's mouth. Thus, tooth sterilization can be carried out using either a recess or cavity 320 or a sealed or open reservoir 316 carrying heated fluid or allowing heating of the carried fluid.

Figure 4:
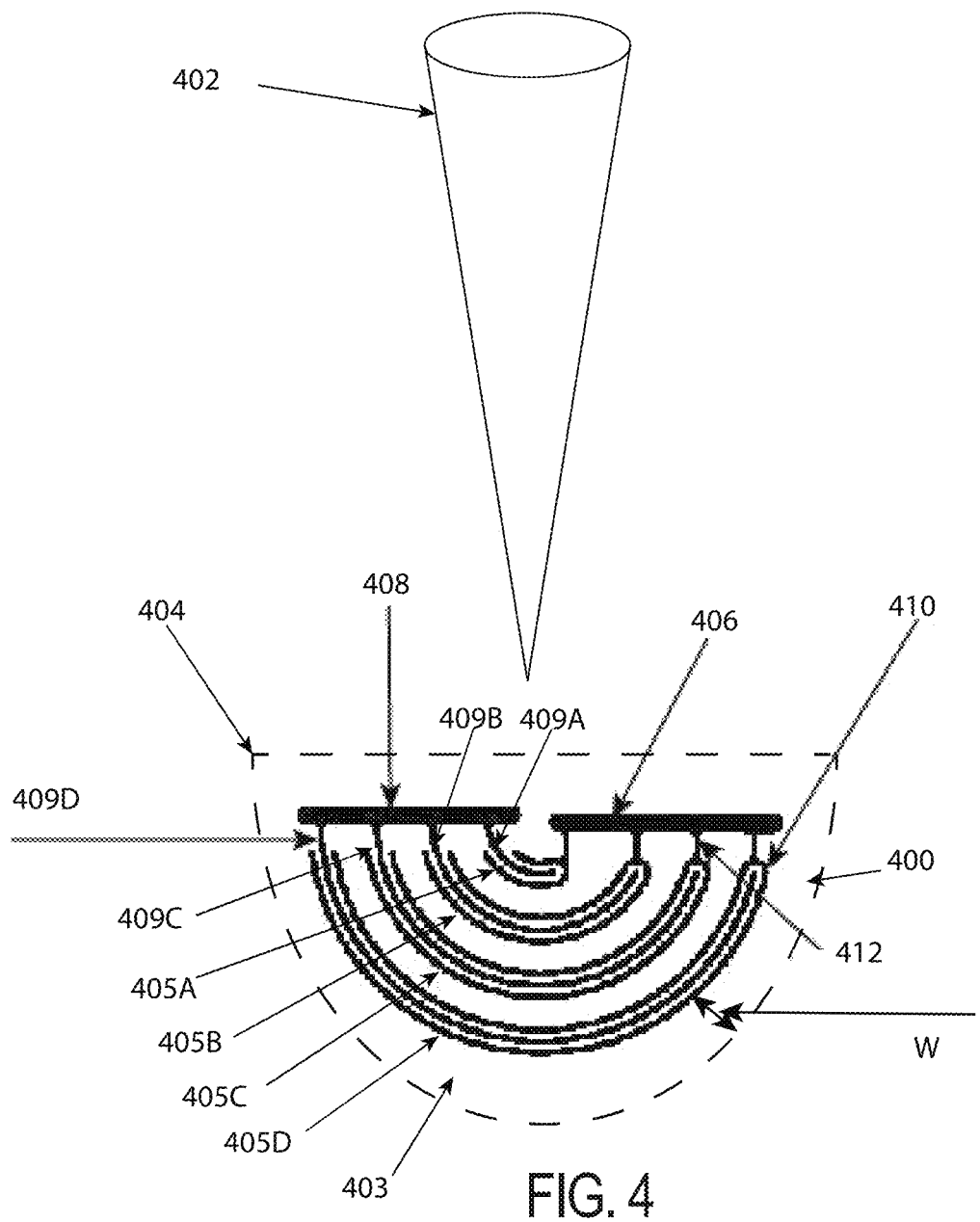
FIG. 4 shows an example of using RF or other electromagnetic energy to apply localized heating to a tooth, such as can include optionally heating a fluid that can be introduced into the root canal of a tooth.

FIG. 4 shows an example of portions of a four zone thin-film or thick-film heating device 300 for using RF or other electromagnetic energy to apply localized heating to a tooth 304, such as directly or optionally by heating a fluid that can be introduced into the root canal of the tooth 304, although introducing a fluid is not required. While four heating zones having corresponding electrically conductive AC electromagnetic input signal structures 405A-D are illustrated in FIG. 4, a different number of zones is possible, such as using the principles illustrated in FIG. 4.

In FIG. 4, a thin conformal active substrate polymer sheet 400 can be arranged as a conical flexible substrate cone 402 that can be sized and shaped to be inserted into a recess or cavity 320 or root canal of a tooth 304. The cone 402 of the conical flexible substrate 400 can have cone dimensions similar to the root canal dimensions illustrated in FIG. 2A. The recess or cavity 320 can be formed in the tooth 304 so as to open into the root canal or other target treatment region of the tooth 304. When the substrate 400 of the cone 402 is cut longitudinally and unfolded to lie in a plane, a periphery 404 of the unrolled and flattened substrate 400 can appear as a semicircle peripheral outline, such as shown in the example of FIG. 4.

The flexible substrate 400 can include a thin sheet of a polymeric or plastic dielectric base material, upon which an electrically conductive AC electromagnetic input signal structure 405 can be formed. The electrically conductive AC electromagnetic input signal structure 405 can include a common mainline 406 and an electrically conductive common ground line 408 that can be printed or otherwise formed on the flexible substrate 400. An apron 403 portion of the substrate 400, having an apron width "W" can extend about the periphery 404 of the unrolled and flattened substrate 400, such as more laterally peripheral than the outer-most zone depicted by its corresponding electrically conductive AC electromagnetic input signal structure 405, and more laterally peripheral than the electrically conductive common ground line 408 and the electrically conductive main line 406. An illustrative example of a suitable flexible substrate 400 is described in: (1) Deo U.S. patent application Ser. No. 18/046,414 entitled CONFORMABLE POLYMER FOR FREQUENCY-SELECTABLE HEATING LOCATIONS, filed Oct. 13, 2022 and published on Apr. 13, 2023 as U.S. Patent Application Publication No. 2023/0111595; and (2) Deo U.S. Provisional Patent Application No. 63/262,477, filed Oct. 13, 2021, entitled CONTROLLABLE HEAT GENERATING PLASTIC AND DEVICES AND METHODS FOR MAKING AND USING SAME SUCH AS FOR PROVIDING FREQUENCY-SELECTED HEATING LOCATION ON CONFORMAL PLASTIC FILM, each of which is hereby incorporated herein by reference in its entirety.

For example, the flexible substrate 400 can be included in an electromagnetic frequency addressable transducer heating device 300, which can include the substrate 400 and the electrically conductive AC electromagnetic input signal structure 405. The substrate 400 can include a polymer base material, such as which can include an electromagnetic energy responsive doping material. The substrate 400 can include multiple layers. Individual ones of the multiple layers can respectively have different material compositions. For example, individual ones of the multiple layers of the substrate 400 can provide different responses to an applied AC electromagnetic input signal, such as which can be received from the control system and AC power source 314 via the instrumentation lead 312.

The electrically conductive AC electromagnetic input signal structure 405 can be arranged directly or indirectly adjacent to the substrate 400. The electrically conductive AC electromagnetic input signal structure 405 can be configured to receive an applied AC electromagnetic input signal, such as for reactively coupling electromagnetic energy into the substrate 400. The electromagnetic energy coupled into the substrate 400 can actuate a heating or other transducer in the substrate 400 in response to the applied AC electromagnetic input signal.

Optionally, the multiple layers of the substrate 400 can include a first layer that can be doped with a first dopant material and a second layer that can be doped with a different second dopant material. The first layer can be more absorptive of electromagnetic energy than the second layer, such as by the different dopings of these layers of the substrate 400. For example, the first dopant material in the first layer can include carbon and the different second dopant material in the second doping layer can include barium titanate. The second layer doped with barium titanate can be located closer to the electrically conductive AC electromagnetic input signal structure 405 than the first layer doped with the carbon first doping material. The second layer can include a material selected to receive and focus received AC electromagnetic energy, and the first layer can include a material selected to absorb AC electromagnetic energy such as to produce heat. Different materials or material combinations than carbon and barium titanate doped base materials may similarly be used. A base material of the substrate 400, or of one or more layers thereof, can include one or more of polyurethane, polyimide, silicone, polycarbonate, or other thermoplastic polymer.

In an example, the polymer base material of the substrate 400 can include a first layer, which can include an electromagnetic energy absorbing first doping material, such as carbon, and a second layer, which can include an electromagnetic energy focusing second doping material, such as barium titanate. In an example, the substrate 400 can include the second doping material in a greater percentage by weight than the first doping material.

The heating device 300 can include a selectively addressable lossy dielectric heating transducer that can be configured to be selectively actuated by tuning a frequency of the AC electromagnetic input signal applied to the electrically conductive AC electromagnetic input signal structure 405. Such selective actuation of one or more individual or groups of heating transducers can be provided by configuring the electrically conductive electromagnetic input structure, printed or otherwise located on the substrate 400, with one or more resonators 410, which can be selectively addressed individually or in groups by establishing or tuning a frequency of the applied AC electromagnetic input signal.

The electrically conductive AC electromagnetic input signal structure 405 can include a mainline 406 (also referred to as the power line) and a ground line 408 that can be electrically connected by a corresponding electrically conductive tap line 412 to one or more electrically conductive resonators 410, which can similarly be printed or otherwise formed on the substrate 400. The tap line 412 and the individual ground lines 409 that can be connected to the common ground line 408 can be electrically connected, such as at respective midpoints of respective portions of the respective resonators 410, such as to form respective terminals for the respective resonators 410. Such an arrangement can help enable applying an AC electrical input signal across the terminals of one or more of the resonators 410 to provide frequency-based control of heating location at specifiable locations along or with respect to the central longitudinal axis of the cone substrate 400. The arrangement shown in FIG. 4 can permit the innermost (e.g., closest to the mainline 406 and the common ground line 408) to the outermost (e.g., furthest from the mainline 406 and the common ground line 408) ones of the resonators 410 to be specifically addressed, individually or in one or more desired groups, such as by specifying or varying the AC frequency of the electrical input signal applied to the mainline 406. The resonators 410 and the other electrical connections are placed or otherwise formed on an active substrate 400, which produces heat at one or more adjustably specifiable locations in the substrate 400 that are frequency-addressable by varying the AC frequency of the electrical input signal, as explained above, as well as in the following patent documents, which are incorporated herein by reference in their entireties: (1) Deo U.S. Pat. No. 9,536,758; (2) Deo U.S. Pat. No. 10,431,478; (3) Deo U.S. Patent Publication No. US 2020-0118846 A1; (4) Deo U.S. Pat. No. 10,515,831; (5) Deo U.S. Patent Publication No. US 2020-0135507 A1; (6) Deo U.S. Pat. No. 10,553,462; (7) Deo U.S. Pat. No. 11,152,232; (8) Deo U.S. Patent Publication No. US 2022-0108899 A1; and (9) Deo U.S. Provisional Patent Application No. 63/262,477.

In a variation of what is shown in FIG. 4, the resonators 410 and their respective individual ground lines 409 can be interchanged. This will have the effect of shorter resonator 410 lines that can be located in between a pair of longer individual ground lines 409. Such a modified arrangement will operate at different resonance frequencies then the version shown in FIG. 4 in which an individual pair of resonator 410 lines are on the outside of an individual ground line 409 located therebetween. A resonator having shorter resonator 410 lines will operate at higher frequencies than a resonator with longer resonator 410 lines.

To recap, FIG. 4 shows an example of a multi-zone heating device using a conformal polymer substrate on which can be located electrically-addressable input structures of individual resonators 410 corresponding to the respective zones of the multiple zones of the multi-zone heating device. Thus, each heating zone can be addressed independently (individually or in a group) by a specified frequency of the AC electrical input signal applied to the electrically conductive input structures associated with a particular resonator 410 of a particular heating zone. The heating device can be configured to operate to produce heat in a single or an individual zone or the entire one or more zones can be active for heating concurrently. The substrate 400 can be made of a single compounded material. The material of the substrate 400 can include an RF or other electromagnetic energy absorber, such as activated carbon nanoparticles that can be mixed into a polymer to form the material of the substrate 400. In case of an RF or other electromagnetic energy absorber that is not addressable by selecting or tuning the frequency of the AC electrical input signal, external switches and independent power paths can be used, but this will add additional cost and complexity that is need needed with a configuration in which the frequency of the applied AC electrical input signal can be established or tuned to select a particular individual resonator or group of resonators. For a device with more than one zone, addressing a zone by establishing or adjusting the frequency of the input signal can therefore be advantageous.

Figure 5A:
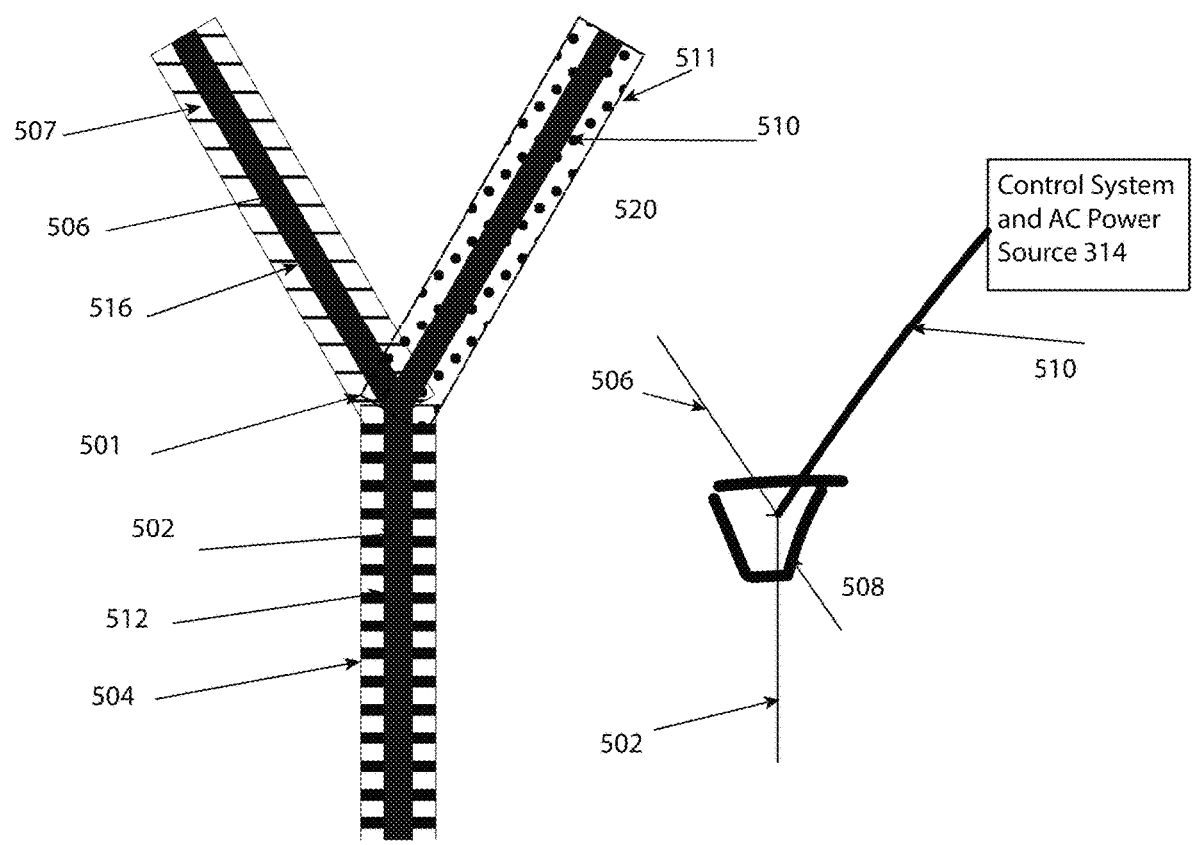
FIGS. 5A, 5B, and 5C show examples of various portions of a heating device.

FIG. 5A shows an example in which a distal portion of the heating device 300 can include a segmented linear arrangement, such as can be segmented in a Y-shape. In the example of FIG. 5A, there are three segments ("legs") 502, 506, and 510 to the Y-shaped arrangement. Each of the legs 502, 506, and 510 can include a respective electrical conductor 512, 516, and 520. The distal working portion 302 of the heating device can include the leg 502, which can include the electrical conductor 512 printed or otherwise formed upon an active substrate 400 as described. The electrical conductors 512 and 516 can be insulated by an insulating material, which need not be the same material as that of the active substrate 400. In FIG. 5A, the three legs 502, 506, and 510 can be physically interconnected, such as at a central intersection location 501 of the Y-shaped arrangement.

The distal working portion 302 of the heating device 300 can include the heating transducer leg 502. The heating transducer leg 502 can include an electrical conductor 512 that can be formed on or coated with an active substrate material 504. The active substrate material 504 can be similar to the material of the active substrate 400 described herein, although it need not be formed into a cone 402. The heating transducer leg 502 can be sized and shaped to be inserted into a tooth cavity, such as into the root canal of a tooth 304. The heating transducer leg 502 can be made of a flexible but sufficiently rigid substrate 504 material to allow the heating transducer leg 502 to be pushed, and thereby inserted, into the root canal. The active substrate material 504 can be shaped such that its length forms an active linear segment region over which heat can be generated within the active substrate material 504 in response to the electrical input signal applied to the electrically conductive terminals and associated resonator 410 structures that are printed onto or otherwise formed upon the active substrate material 504, such as similarly described herein.

The grounded resonator leg 506 can include an electrical conductor 516 that can be formed on or coated with an electrically insulating second material 507—which can be a different material than the active substrate material 504, because no heat is needed to be generated in the grounded resonator leg 506, which can serve to provide a return path for the applied AC electrical input signal. In view of the limited space within the root canal, the grounded resonator leg 506 can be sized and shaped to be located outside of the root canal and connected to a ground terminal of the control system and power source 314, such as via the instrumentation lead 312 or via a separate ground lead. The grounded resonator leg can 506 remain outside of the tooth while the heating transducer leg 502 is inserted into the root canal or other tooth cavity. Because the grounded resonator leg 506 need not be pushed into the root canal, it can be made of a material that can be more flexible (less rigid) than the heating transducer leg 502, if desired.

The instrumentation lead leg 510 can be sized and shaped to extend outward for interconnection of its electrical conductor 520 with a power signal output terminal of the control system and AC power source 314, such as via the instrumentation lead 312. The power signal output of the control system and AC power source 314 can provide an AC electromagnetic energy input signal, which can also be referred to as a power signal. The AC electromagnetic energy input signal can be frequency-tuned to select a desired heating location in the active substrate material 504 along the heating transducer leg 502, as explained herein. Such control circuitry of the control system and AC power source 314 can be located outside of the subject's mouth.

The instrumentation lead leg 510 can include an electrically conductive material of an electrical conductor 520 that can be coated with or formed upon an electrically insulating dielectric material 511. At the control circuitry 314, the electrical conductor 520 of the instrumentation lead leg 510 can be electrically connected to the external power source included in or coupled to the control circuitry 400. In such a configuration, the heating transducer leg 502 can provide a partially ungrounded segment that produces heat in the active substrate 504 coating the electrical conductor 512 in the heating transducer leg 502 in response to the applied AC electrical input signal being applied to the electrical conductor 512 via the electrical conductor 520.

Figure 5C:
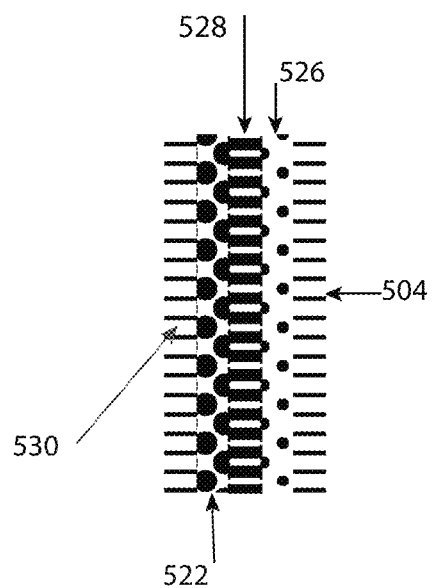
Figure 5B:
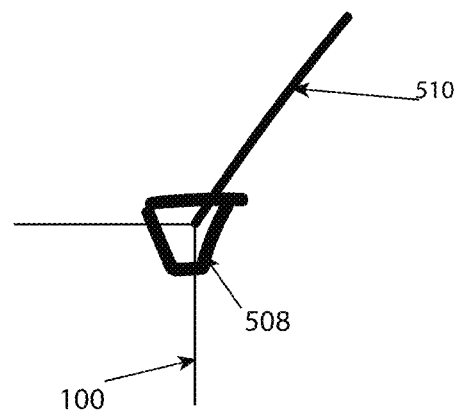

In FIG. 5B, an optional plug or fluid reservoir 508 can be positioned or located outside of the root canal. As shown in FIG. 5B, a small plug (e.g., similar to a conical or frusto-conical button or stopper) of the fluid reservoir 508 can be placed at the intersection of the three segments, legs 506, 502, and 510, in this configuration. When the heating transducer leg 502 is inserted into the root canal, the plug 508 at the intersection of the three segments 506, 502, and 510 can be used to seal the opening of the root canal, such as to help hold heat or heated fluid within the root canal while the heat treatment is being applied.

FIG. 5C shows an example of a portion of distal working portion 302 of the heating device 300 such as can include the heating transducer leg 502. The heating transducer leg 502 can include an electrically conductive input structure that can include an electrical power plane conductor 512 that can be a layer of a multi-layer structure that can be formed on or coated with an active substrate material 504. In the example of FIG. 5C, the active substrate 504 can include a multi-layer structure formed thereupon, such as which can include: (1) a ground plane 526 that can be electrically connected to the ground conductor 516 of the ground leg 506; (2) a power plane 522 that can include or be electrically connected to the electrical conductor 512 and also connected to the control circuitry and power source 314, such as via the electrical conductor 520 of the instrumentation lead leg 510; (3) a capacitive dielectric plane 528, such as can be interposed between the ground plane 526 and the power plane 522; and (4) an electrically insulating layer 530, which can be located adjacent to the power plane 522 on a side that is opposite from the capacitive dielectric plane 528. The electrically insulating layer 530 can be made of the same material as the active substrate 504 or 400, such as where heating is also desired to occur in the electrically insulating layer 530, or it can be made of a different material that has electrically insulating properties, but which does not have doping or other characteristics to enhance heat production therein.

FIGS. 5D, 5E show two illustrative examples in which a distal portion of the heating device 300 can include a Y-shape, similar to that described above with respect to FIG. 5A. However, in FIG. 5D and FIG. 5E, the distal leg 522 providing the heating transducer to convert AC electromagnetic signal energy to heat can include the ground conductor 516 being a wire that can be spirally wound about and affixed to an lossy active dielectric substrate 400 that can be formed as an elongate member. In FIG. 5E, the distal leg 522 can include the elongate lossy active dielectric substrate 400 elongate member being spirally wound about and affixed to the ground conductor 516.

Figure 6:
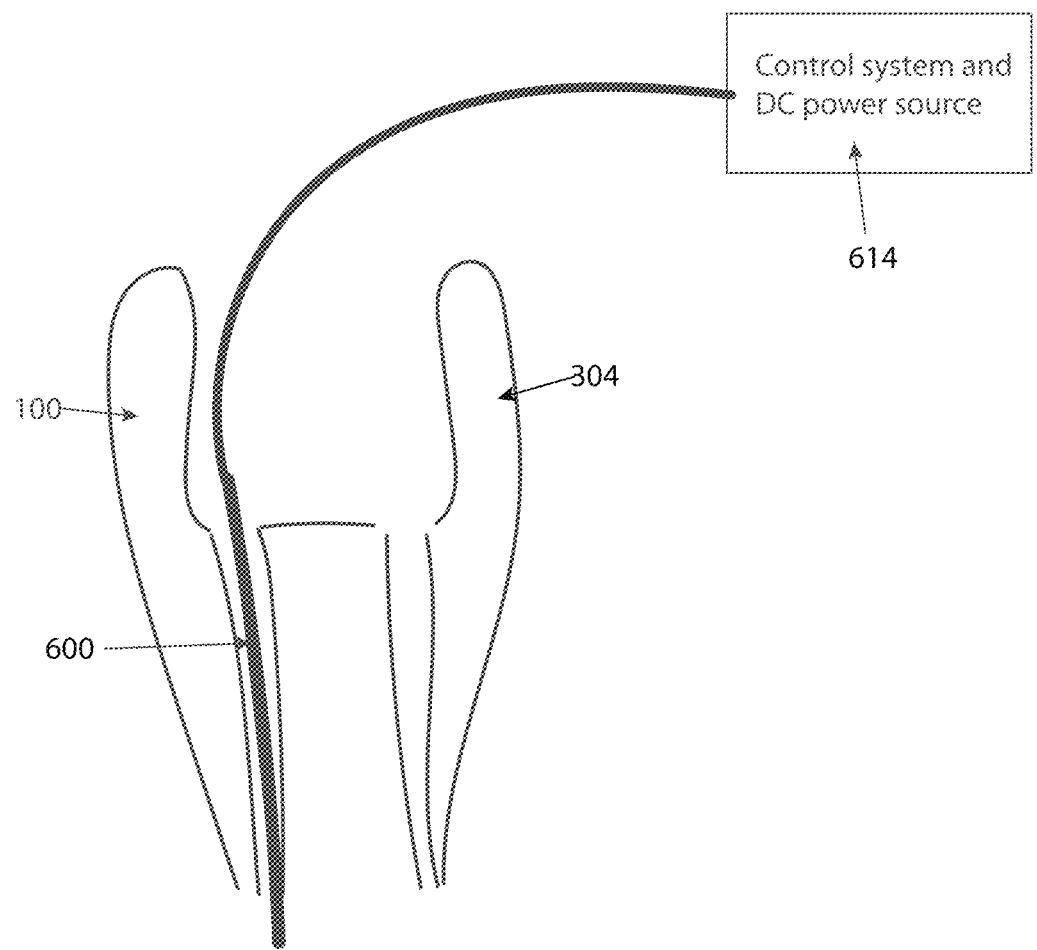
FIG. 6 shows an example in which a DC resistive or Joule heating element can be placed inside the root canal for heat treatment.

FIG. 6 shows an example in which the heating transducer can include a DC resistive or Joule heating element 600 can additionally or alternatively be placed inside the root canal and electrically connected to and controlled by an appropriate DC electrical energy control system 614. The heating element 600 can include or can be provided together with a temperature sensor, which can be included a feedback loop of the control system 614. The feedback loop can be used to measure the temperature inside the root canal and, in response, to adjust the applied energy delivered to the DC resistive or Joule heating element 600 to obtain the desired temperature inside the root canal. The DC resistive or Joule heating approach can be used additionally or alternatively to the RF electromagnetic energy heating approach described above with respect to FIG. 4 and further described in the above-incorporated U.S. patent documents, which can also use feedback control to control the applied localized heating based on a temperature sensor such as which can be located on the substrate of the heating transducer leg 502 and placed inside of the root canal.

Figure 7:
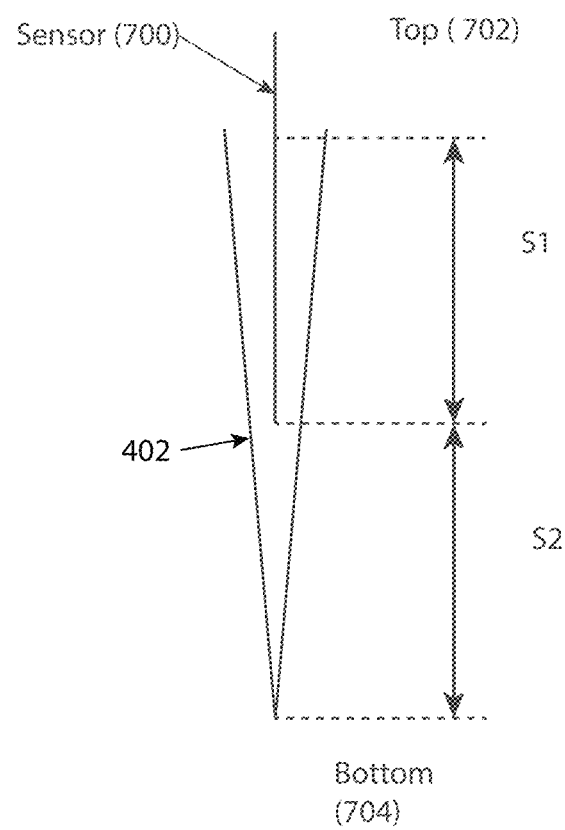
FIG. 7 shows an example of a temperature sensor that can be used for sensing or measuring local temperature in the root canal, such as during treatment to control heat delivery based at least in part on the measured temperature.

FIG. 7 shows an example of a temperature sensor 700, such as which can be placed inside of the root canal or other tooth cavity in which a transient thermal cell is being provided for dental heat treatment. The temperature sensor 700 can be separate and independent from the heating device 300 or it can be included with the distal working portion 302 of the heating device 300. In an example, the temperature sensor 700 can additionally or alternatively be placed along a central longitudinal axis of the heating device 300 having the substrate 400 shaped as a cone 402, such as at with a distal tip of the temperature sensor located at a distance of S1 from the proximal or coronal (top 702) end of the cone 402 and located at a distance of S2 from the distal or apical (bottom 704) end tip of the cone 402 having the conical substrate 400. The distal tip location of the temperature sensor 700 can be the temperature measuring locus of the temperature sensor that can be used to measure a temperature at the placement location of the distal tip of the temperature sensor 700. The measured temperature from the temperature sensor 700 can be used to calibrate or re-calibrate or adjust the heating being provided, such as in a feedback control loop. This can be helpful, such as in situations in which the system is placed in an environment in which the effective dielectric constant of the environment is changing. It may be desirable to locate the temperature sensor 700 at an appropriate sensor depth within the tooth root canal or tooth, for example, as deep as possible within the root canal. The geometry of the root canal may affect the achievable depth at which the temperature sensor 700 can be placed. Multiple temperature sensors 700 can be provided. For example, a first temperature sensor 700 can optionally be placed within the tooth root canal or tooth cavity, such as at or near the target region to be treated, such as to monitor the treatment temperature. A second temperature sensor can optionally be placed at safety monitoring location outside of the tooth, such as against the cementum, such as to monitor temperature at the safety monitoring location to help ensure that it remains within the safety temperature range, such as described herein.

The heating device 300 can create heat and can also concurrently serve as a temperature sensor for measuring temperature. The effective dielectric "constant" seen by the heating device 300 is a property of the materials of the heating device 300 and the environment in which it is being used. The effective dielectric constant can change with temperature, which can alter the amount of power being delivered to the target and the resonance frequency of a resonator 410 being used to deliver power to the active substrate 400 for being transduced into heat for the dental treatment. Therefore, the resonance frequency (or shift in resonance frequency) can be used as a proxy indication for a change in temperature. For a biological structure, such as a tooth root canal, the effective dielectric constant can change appreciably due to a change in external material characteristics, such as denaturing of the biofilm or water content, some of which are correlative to temperature. Regardless of whether the change in dielectric constant is due to temperature, or due to secondary factors that are affected by heating and a change in temperature, such resonance frequency shift information can be used to calibrate the heating device 300 or in a closed control loop to control operating the heating device 300. Error due to change in effective dielectric constant can be calculated by the control circuitry and power source 314. If the change in effective dielectric constant is large enough, re-calibration of adjustment of one or more system parameters can be made in response. The location of the distal end tip of the temperature sensor 700, as shown in FIG. 7 with respect to S1 and S2, can be helpful to understanding or assessing the thermal fields in the tooth 304.

Figure 8:
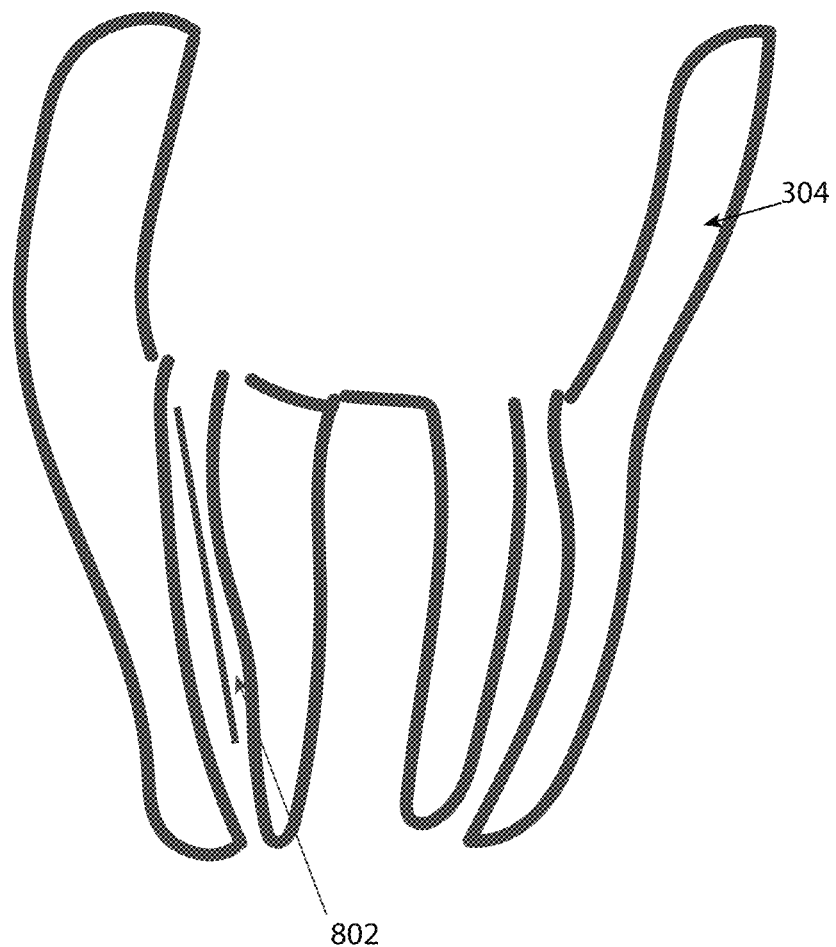
FIG. 8 shows an example in which a radioactive seed can be placed inside the root canal to provide radioactive disinfection of the root canal.

FIG. 8 shows an example in which a radioactive seed 802 (e.g., such as can include cesium 131 with a half-life of about 9 days) can be placed inside the root canal and left there to provide radioactive disinfection of the root canal. For example, over 9 days the radioactive material can slowly disinfect the entire root canal system. The radioactive seed 802 may be left there inside of the root canal permanently, if desired.

Figure 9A:
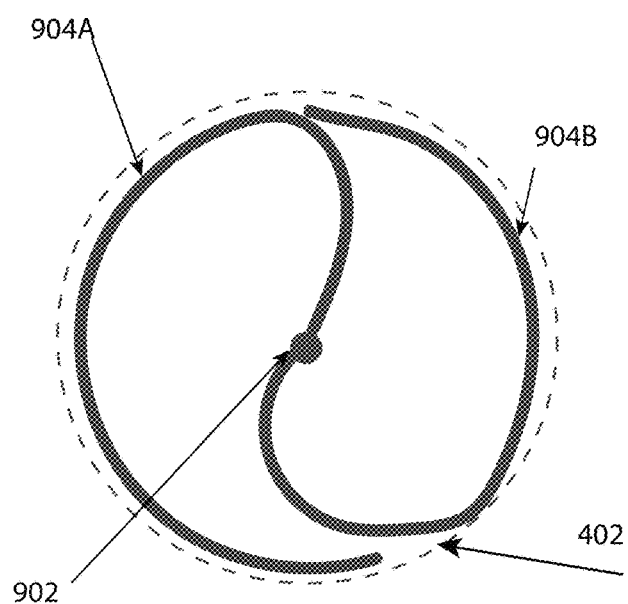
FIGS. 9A and 9B show an example of an overall layout of the entire thin film cone substrate of an example of a distal portion of the tooth root canal heating device.
Figure 9B:
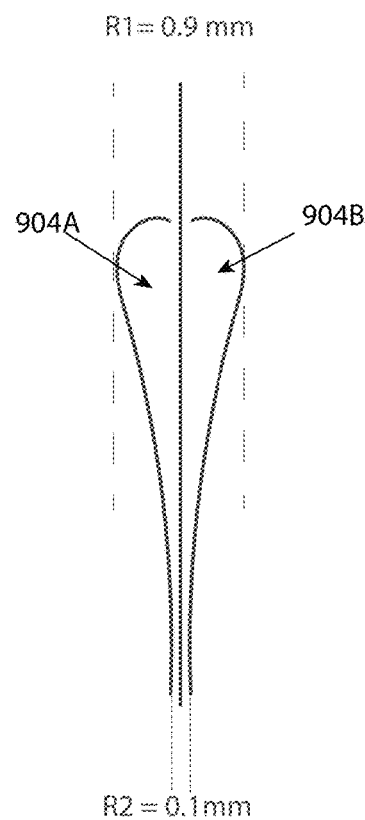
Figure 9B:
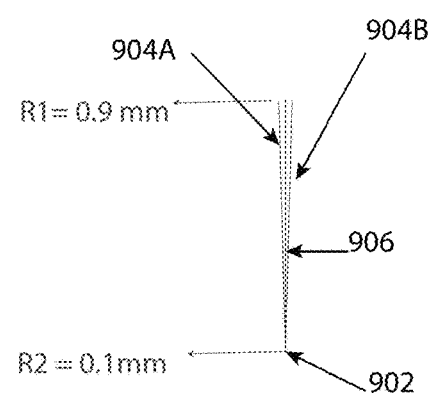
Figure 9C:
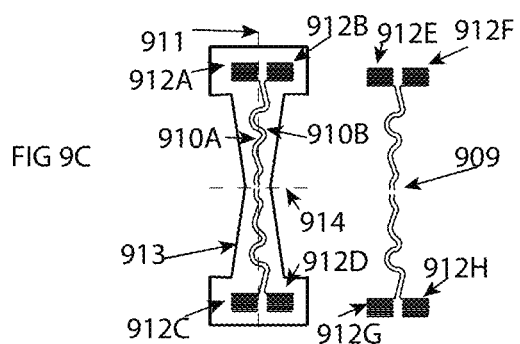

FIGS. 9A, 9B, and 9C show an example of an overall layout of the entire thin film substrate 400, such as can include a cone 402 or similar folded or rolled or other cone-like structure, of the tooth root canal heating device 300. In the top view of FIG. 9A, the cone 402 that can be formed using the thin film cone substrate 400 can include a central distal tip 902 and flexible opposing "butterfly" wings or lobes or flaps 904A-B that can be wrapped around a central longitudinal axis around to form a generally conically-shaped arrangement that can conform to the interior sides of the root canal of the tooth to be treated. In the side view of FIG. 9B, and unrolled and flattened planar version is shown, with the two wings 904A-B oppositely extending laterally from a central longitudinal axis, which is depicted by a line 906 in FIG. 9B. The two wings 904A-B can extend more broadly laterally near a proximal end and can extend less broadly laterally near a distal end, such as to help ease insertion and to better permit the conformed shape to conform to an interior shape of the root canal or tooth cavity. The two wings 904A-B can be made of a polymer or other flexible substrate material, such as described herein. The material can be flexible enough to permit the two wings 904A-B to wrap around inside the root canal and to be somewhat unfurled to conform against the interior walls of the root canal of the tooth when placed in the root canal or other tooth cavity. In an illustrative example of the flattened planar arrangement shown in FIG. 9B, an unrolled and flattened distal tip portion of the thin film substrate 400 can be rolled into a cone 402 having a distal end tip portion that can fit within a lateral diameter of 0.1 millimeters. An unrolled and flattened proximal end portion of the thin film cone substrate 400 can fit within a lateral diameter of 0.9 millimeters. Thus, the lateral dimension can be tapered from a larger dimension at a proximal end of the substrate 400 that can be rolled into a cone 402 to a smaller dimension at a distal end of the substrate 400 that can be rolled into the cone 402. Such an approach can offer a potential advantage in that the distal working portion 302 of the heating device 300 can be rotatably inserted into the root canal or other tooth cavity, in a similar manner to a flexible "screw." Rotating during insertion into the root canal or other tooth cavity makes inserting the distal working portion 302 of the heating device 300 easier and can help enables an even spreading or unfurling of the substrate 400 after inserting, such as compared to a direct plunging insertion without rotating during insertion. Rotating during inserting can also help inhibit or prevent perforation or damage to the distal working portion 302 of the heating device 300 during insertion.

FIG. 9C shows an example of a serpentine pattern of a pair of side-by-side electrically conductive traces 910A-B, such as which can be placed on the substrate 400, such as extending along and defining a central longitudinal axis 911 between respective electrically conductive terminals 912. A horizontal axis 914 can be defined between the end terminals. An apron 913 can represent the portion of the substrate 400 that extends laterally outward beyond the electrical traces that are printed or formed on the substrate 400. The serpentine pattern in FIG. 9C is narrow toward the center of the serpentine pattern along its longitudinal axis. FIG. 9C shows two such serpentine patterns arranged along the longitudinal axis, with a gap between locations of the electrically conductive traces toward the center (e.g., toward the horizontal axis 914) of the serpentine pattern. The gap can include a "shortest" distance between the two electrically conductive traces that can vary along different locations along the length of these electrically conductive traces. A desired locus of heat generation along the length of these electrically conductive traces can be selected by establishing or tuning an AC frequency of an AC electrical input signal applied to the inputs of these electrically conductive traces, such as to a resonance or other peak energy transfer frequency at a particular location, along the length of these electrically conductive traces, that is associated with a particular "shortest distance" gap or minimum spacing between the two electrically conductive traces, such as described in U.S. Pat. Nos. 9,536,758, 10,431,478, and 11,610,791, each of which is incorporated herein by reference in its entirety, including its description of selectively addressing locations along a length of a pair of electrode traces.

Thus, in the example of FIG. 9C, the distal end portions 302 of a pair of two separate heating devices can be located next to each other. The structure of a first one of the pair can be a mirror image of the second one of the pair, mirrored across the central horizontal axis 914. The distal end portion 302 of the heating device 300 can be folded across the central horizontal axis 914 and then placed into the root canal or other tooth cavity. A temporary or permanent elongate guide member may be placed along the central longitudinal axis 911, such as after folding. A tip of the guide member can be located at the center or horizontal axis 914. The guide member can be used as a "plunger," such as to help push the distal end portion 302 of the heating device 300 into the root canal or other tooth cavity. The guide member can also optionally be used to optionally help pull the distal end portion 302 of the heating device 300 out of the root canal or other tooth cavity, such as after treatment. Including a lateral barb or protrusion at or near a distal tip of the guide member can help facilitate engaging the distal end portion 302 of the heating device 300 for such removal.

Figure 9D:
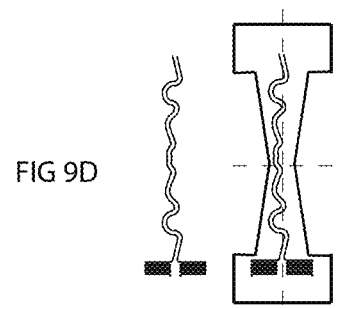

FIG. 9D shows an example of a single serpentine pattern of electrically conductive traces of a similar shape, such as which can be located on the substrate 400. However, in this example, the electrically conductive traces can be electrically connected to each other toward the center of the serpentine pattern. Comparing FIGS. 9C and 9D, it can be seen that there are two separate power inputs to the individual heating devices shown in FIG. 9C. By contrast, in the example of FIG. 9D shows a unified heating device that can employ a single power connection. The arrangement shown in FIG. 9C can help enable powering the distal working portion 302 of the heating device 300 from either one of—or from both—of the ends. The arrangement shown in FIG. 9C can also enable providing a ground plane at each of the ends. Thus, the arrangement shown in FIG. 9C can help enable delivering a greater amount of power (and heat) to the desired target location relative to the arrangement shown in FIG. 9D.

In both FIGS. 9C and 9D, the substrate 400 upon which the electrical traces can be formed can be folded in half along the central horizontal axis 914 and then can be inserted into the root of the tooth. The apron 913 portion of the substrate 400 can be cut along the central longitudinal axis 911 such that the distal working portion 302 of the heating device 300 can assume an outer shape such as shown in FIG. 9A. The width of the gap 909 along the central horizontal axis 914 at a central location along the central longitudinal axis 911 can be about 1 millimeter. Thus, when folded an inserted, the gap 909 will yield a spacing between about 700 micrometers and 1 millimeter between (1) the ends of the electrical conductors shown in FIG. 9C as abutting the gap 909 and (2) an apical tip of the folded distal working portion 302 of the heating device 300. In such an illustrative example, the active heating region can begin at a location that is about 700 micrometers to 1 millimeter away from the apical tip of the folded distal working portion 302 of the heating device 300. However, exact dimensions may differ depending on the size and morphology of the tooth being treated. In FIGS. 9C and 9D, the total width across both of the adjacent serpentine electrically conductive strands can be about 200 micrometers. This can accommodate insertion and use within the average diameter at a coronal end of the root canal. This can provide a cone 402 of the approximate size of the root canal. The entire flexible conformal active heating substrate 400 of the heating device can be sized and shaped to allow the distal working portion 302 of the heating device 300 to be inserted toward the apical end of the root of the tooth.

Figure 9E:
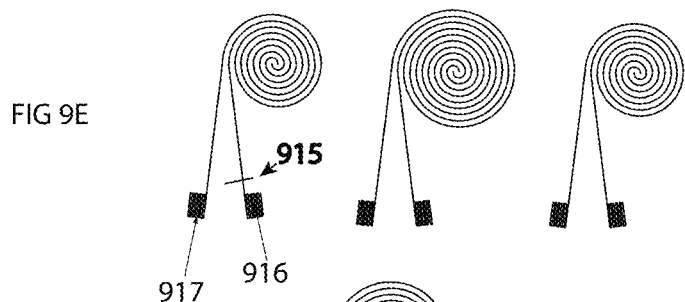

FIG. 9E shows a set of spiral patterns of electrically conductive traces coupled to electrically conductive terminals, such as can be printed on or otherwise formed upon a disk that can be shaped into a cone 402 or other shape using the conformal polymer active substrate 400 material. In the example of FIG. 9E, the different spirals can have different diameters, a different number of spiral turns or loops, or both. The different diameters can be specified so the radius of the spiral from its center point to its lateral periphery can equal and define the active length of the heating device. The active length is the longitudinal length within the root along which heat is created after the cone-shaped distal working portion 302 of the heating device 300 is inserted into the root. The distal working portion 302 of the heating device 300 can be placed into the root canal or other tooth cavity, such as with the center of spiral shown in FIG. 9E forming the apical end tip. The disk (when flattened) generally becomes a cone or takes shape of the root when placed into the root or the other tooth cavity, such as with a center of the spiral forming an apex of the cone 402. Electrical power can be delivered via a power terminal 916 with a return path provided by the ground terminal 917. A stub filter 915 can optionally be provided along the electrically conductive signal pathway connected to the power terminal 916. The stub filter 915 can help filter out noise that may be present on the electrical input signal, such as at frequencies other than the resonance frequency of the resonator or resonators to be addressed and actuated using the electrical input signal. The spacing between the electrical traces extending from the respective power terminal 916 and the ground terminal 917 can be such that heating is generated at desired locations, and avoided at undesired locations. For example, the traces can splay apart near their respective terminals to avoid heating in those regions, but can be located equidistant from each other throughout a portion at which heating is desired. The electrical traces can also have a variable minimum spacing therebetween to permit selective addressing of heating transducer locations by adjusting the frequency of the applied AC electromagnetic input signal, such as described or incorporated by reference herein.

Figure 9F:
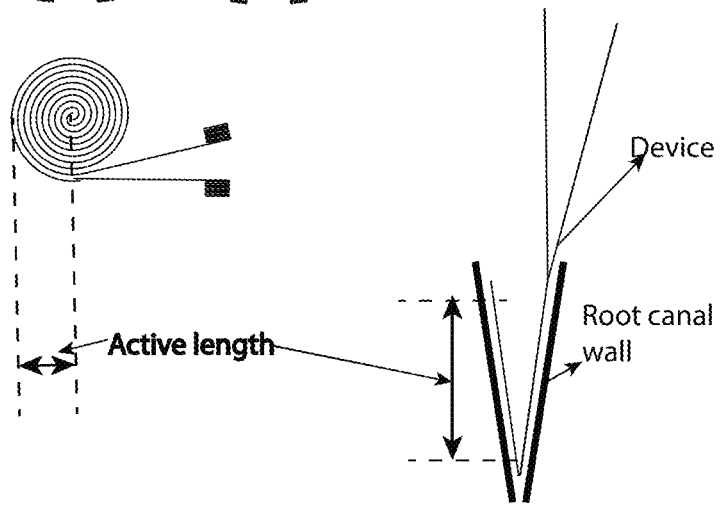

FIG. 9F shows a schematic example of an inserted cone, folded from the flattened circular spiral disk, with the two electrical input electrical conductor strands respectively coupled to the power terminal 916 and to the ground terminal 917.

FIG. 9G shows a schematic example of a multiple zone configuration, such as a two zone pattern. In such a configuration, the electrical trace can include two different resonator structures, such as resonators 930, 940 that have corresponding resonance frequencies such that they can be addressed at two different applied electrical input signal frequencies. For example, an electrical input signal at a frequency of 500 MHz can be used for selectively addressing and actuating a first one of the resonators, such as the resonator 930 such as can have a resonance frequency that is at or near 500 MHz, and an electrical input signal at a frequency of 2 GHz can be used for selectively addressing and actuating a second one of the resonators, such as the resonator 940 such as can have a resonance frequency that is at or near 2 GHz. Providing two or more separately addressable resonators can permit selective activation of such separately addressable resonators by establishing or adjusting the frequency of the applied electrical input signal, such as to match the resonance frequency of the resonator to be addressed and employed for heat generation. This can provide an ability to alter the locus of heat generation, which can help further focus the heat inside of the root canal of the tooth, such as at one or more desired locations. Providing and using multiple zones can help provide better thermal control at the target, such as within the tooth root or other tooth cavity. A main line 935 can be used to deliver the electrical input signal to both of the resonators. A ground line 950 can provide a grounded return path for the electrical input signal provided to both of the resonators. Connection stubs 951 and 952 can be used to tune the resonance frequency for the corresponding resonator and zone to which the particular one of the connection stubs 951 and 952 is connected or otherwise coupled.

Figure 9H:
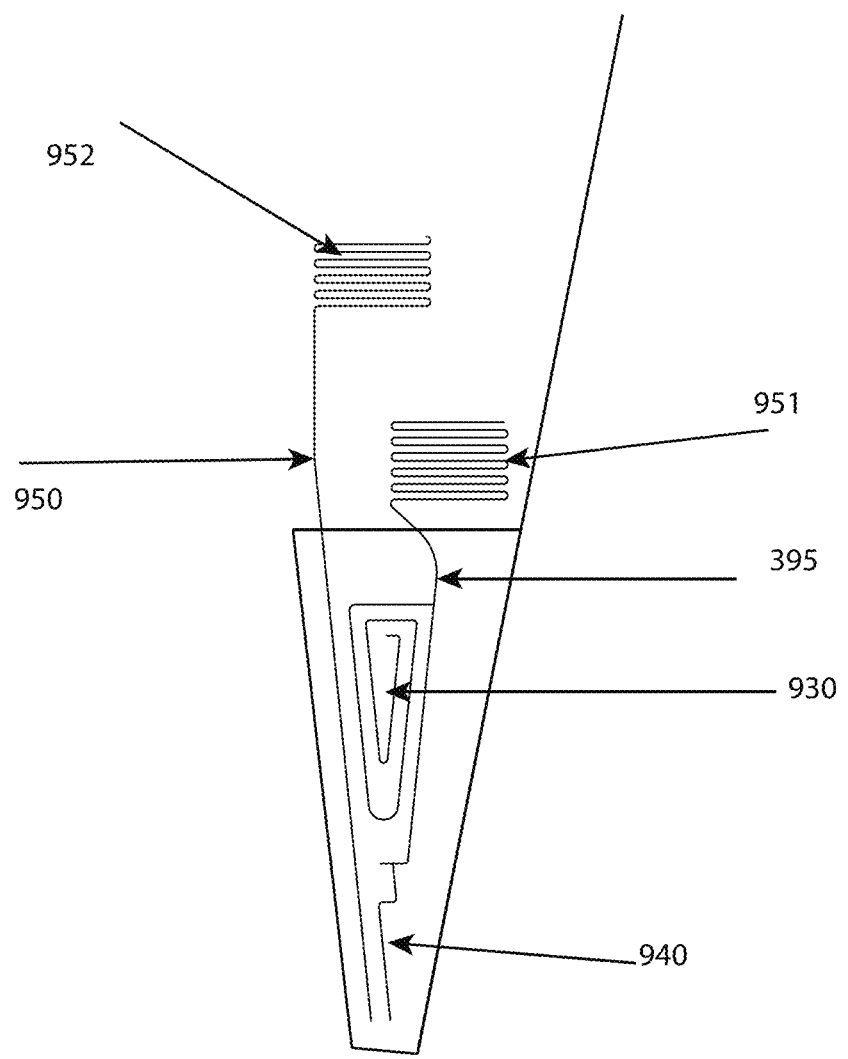

FIG. 9H is an example, similar to FIG. 9G, but also showing an example of a connection tab that can be included for placing the device, such as the multi-resonator device of FIG. 9G. In FIG. 9H, the connection tab can include one or more electrically conductive traces or terminals, such as for connecting to the control system 314.

Figure 10:
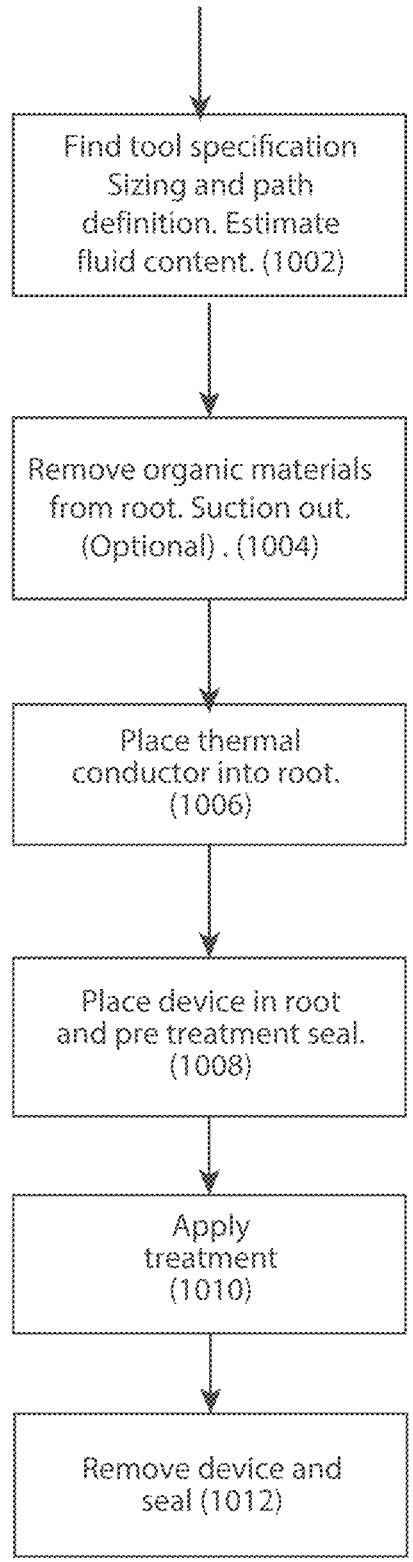
FIG. 10 is a diagram illustrating, among other things, an example of portions of a method of using the thin film cone substrate or other similar localized heating device such as described herein, such as to help disinfect a root canal of a tooth.

FIG. 10 is a diagram illustrating, among other things, portions of a method of using the heating device 300 described herein, such as to help disinfect a root canal of a tooth. In an example, the process 1000 can begin after an endodontist or dentist or other clinician has achieved access to the root canal to be treated, which can include, but need not require any drilling inside the root canal.

At 1002, the clinician can use a root canal mapping tool to measure the minimum diameter of the root canal structure, and the location of this minimum diameter point along the length of the root canal. The root canal mapping tool can have a tool size with a maximum tool diameter that passes through the root canal all the way from its proximal end to its distal end. The root canal mapping tool may optionally include a coating that gets scraped to demarcate the location along the length of the tool that corresponds to the minimum diameter of the root canal. The information developed at 1002 can be used to map to, identify, and select an appropriate disinfection treatment tool. For example, a color coded treatment plan map can be used to translate information developed at 1002 to allow the clinician to pick an appropriate disinfection treatment tool. The appropriate disinfection treatment tool can be selected from a kit providing a plurality of available disinfection treatment tools, such as of different dimensions appropriate for different root canal sizes and morphologies, such as shown in the example of FIGS. 2A, 2B. Once the root canal mapping tool is pulled out of the root canal, the root canal mapping tool can be used to smear whatever biological material from the root canal that is stuck onto the tool onto a microscope slide. The general texture of the spread-out biological material can help the clinician assess or characterize the material in the root canal. For example, fluid content inside of the infected root canal can be assessed by visually inspection, which can optionally involve comparing the smear to sample pictures of smears that can be provided with the kit. Imaging and image-processing capability can be provided to help with this purpose, which can involve an image-processing artificial intelligence (AI) or machine learning (ML) model that can be trained with images of spread material extracted from root canals, such as to provide a ground truth basis for training the learning model.

At 1004, once the root canal size and the fluid content have been determined, the clinician may choose to physically suction out the contents of the root canal. If the fluid content in the root canal is below the amount desired for successful heat treatment to disinfect the root canal, the clinician can suction out internal organic material and fluid in the root canal, and can introduce additional fluid into the root canal, if desired.

At 1006, a liquid or other fluid can optionally be injected into the root canal, such as via a syringe and needle. The injected fluid can include water, saline, or a specialized thermally conductive fluid. Once the root canal is ready to receive the heat treatment device, the clinician can insert an appropriately preselected heat treatment device into the root canal, such as described herein. The heat treatment device can reside on a flexible thin substrate, such as described herein. A plug or sealant may be applied to the root canal opening, such as to help retain heated fluid within the root canal for providing the desired heat disinfection treatment of the root canal.

At 1008, if it is desired that multiple infected root canals be treated concurrently, then the various root canals to be treated can be similarly prepared and distal working end portions of heat treatment devices 300 can be similarly introduced into the desired locations of the root canals. The heat treatment devices 300 can be connected to heat treatment controller circuitry, such as the control system and AC power source 314, which can be controlled by the clinician via a user-interface that can be included in or coupled to the heat treatment controller circuitry 314. Once all the root canals to be treated are prepared and the corresponding heat treatment devices are placed at the desired locations, then the heat treatment devices can then be connected to the treatment controller circuitry 314, which can be included in a treatment control box. A plug or sealant can then be placed at the proximal end of each one of the root canals. This can help inhibit or prevent the heated fluid from seeping out, which can help increase treatment efficacy and efficiency. Such a plug or seal can be achieved by individually tapping on a caulking mechanism with each one of the tools or by applying a sealing solution, such as using a syringe. The sealing solution can be deposited at the intersection between the root of the tooth and the heat treatment device.

At 1010, once a seal is in place, the clinician can trigger heat generation via the graphical user interface provided with the heat treatment controller box that can include the treatment controller circuitry 314. Then, the clinician can wait for the duration of the sterilization procedure to apply the appropriate heat level for an appropriate duration to obtain the desired sterilization of an infected root canal.

At 1012, upon completion of the sterilizing heat treatment of the one or more root canals, the heat treatment devices can be removed. If desired, any biological material that is stuck on the removed heat treatment device can be smeared on a microscope slide or otherwise used for pathology analysis. Once the heat treatment devices have been removed from their placement at the root canal(s), the root canal can optionally be cleaned, such as via irrigation, and any cavities formed in the tooth can be filled and closed, such as using normal root canal procedure closure techniques.

Figure 11:
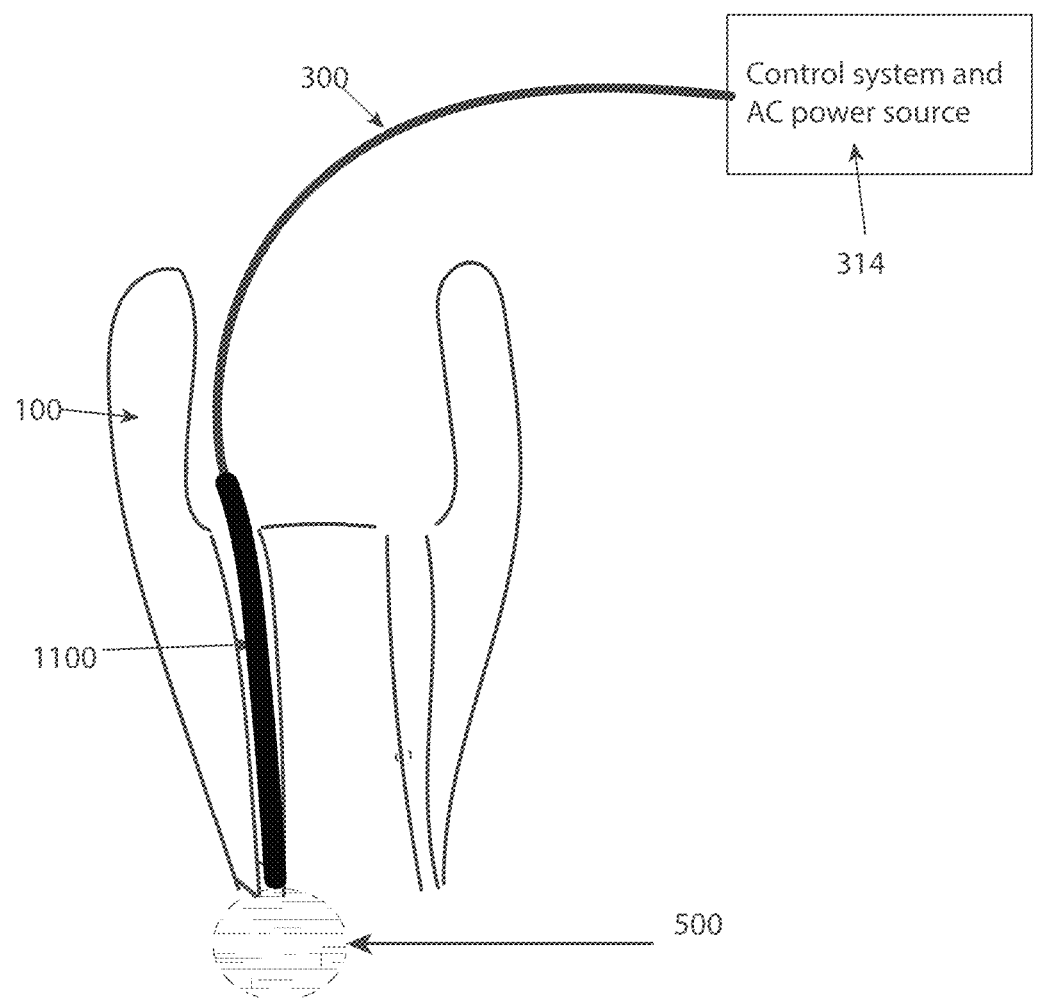
FIG. 11 shows an example of using an RF ablation antenna that can be inserted into the root canal.

FIG. 11 shows the use of an RF ablation antenna 1100 that can be inserted into the root canal. In the example of FIG. 11, instead of (or in addition to) providing localized heating to disinfect an infected root canal, radiofrequency or other electromagnetic energy can be transmitted out of the RF ablation antenna 1100 to heat the material surrounding the RF ablation antenna 1100, thereby disinfecting such material surrounding the RF ablation antenna 1100. Similarly, light (e.g., ultraviolet (UV) or InfraRed (IR)) can be introduced into the root canal, such as via an optical fiber or bundle of optical fibers, such as to help achieve the desired disinfection of the infected root canal.

FIG. 12 shows an example of a heating device 300 as inserted into a root canal of a tooth and connected to an electrical control system 314. In FIG. 12, some ancillary components of the system are also shown. One or more optional spacers 1202 can be used, such as to space the gum away from the tooth 304 during heat treatment of the tooth 304, such as to further protect the gum tissue from heating effects. A temperature sensor 700 can be placed at a desired target location such as in contact with or in proximity to the cementum of the tooth root being treated, such as to monitor temperature outside of the tooth. Such measured temperature information from the temperature sensor 700 can be used to control the applying of heat to the interior of the tooth to allow regions around the exterior of the tooth to remain at safe temperatures during heat disinfection or heat sealing of the tooth. A clip 1204 can be placed upon the tooth, such as to help stabilize or support one or more of the heating device 300, an electrical instrumentation lead 312 that can be connected to the heating device 300, or a rubber or other elastomeric dam 1206 that can be placed over the tooth 304, such as while applying the heat treatment or while performing other treatment on the target region of the tooth 304.

In-vitro experiments of heat treatment of target regions of a tooth were carried out, including at least four separate experiments on previously-extracted teeth to help verify the dental treatment techniques described herein. Each of the previously-extracted teeth used in the experiments was first prepared by an endodontist using drilling, grinding, filing, or other preparation techniques used by an endodontist to provide access to the root canal of the tooth. In some cases, the apical end of the tooth was opened using a 200-micron diameter file. In other cases, the apical end of the tooth was left in its natural state.

Experiment 1 was performed on a single uninfected tooth. A DC power source was used to energize a 100 micron diameter coated nichrome wire that was spirally wound about a rubber core or mandrel. Temperature was measured on an outside surface of the tooth, using a K-type thermocouple and a fiber optic temperature sensor. When a maximum power DC electrical input of 12.5 volts and 0.2 amperes was delivered via the device to the interior of the tooth, the temperature on the outside surface of the tooth did not increase significantly. A FLIR camera was also used to observe the thermal gradient within the tooth, which was clearly visible on the images provided by the FLIR camera.

Experiment 2 was performed using a radiofrequency AC-powered linear device having an antenna portion inserted into the root canal of multiple teeth, which were pre-inoculated with *Staphylococcus aureus*, and which were prepared with an open apical end of the tooth. A distal portion of the AC-powered linear heating device was placed inside of the tooth. Duration and power of an applied AC electrical input signal were varied. Each treated tooth was then broken, stained, and the exposed dentine was visually studied under a microscope. During the entire duration of applying heat within the interior region of the tooth, the outside temperature at the cementum and the enamel was measured using a 300-micron diameter fiber optic temperature sensor, and confirmed that the external temperature remained safely less than 55 degrees C. A microscopic image used to observe the results of this experiment. A control was provided in the form of a tooth sample inoculated with the bacteria, but unstained. It was observed that the stained biofilm present in the dentine was visible under the microscope. The image of the treated section of the tooth shows two samples for two separate teeth, one sample tooth treated with 5 W of power for 1 min and another sample tooth treated with 5 W of power for 3 mins. After 1 minute of heat treatment, some bacteria remain in the dentin. After 3 minutes of heat treatment, all bacteria appeared dead such that no stain was visible.

Experiments 3 and 4 use two versions of thin film heating devices, such as shown in FIGS. 9A-9H, on two different active polymer conformal substrates. Experiment 3 used an active polymer substrate material with a hardness durometer D and a softening temperature of 63 degrees C. Experiment 4 used a hardness durometer A and a 58 degree C. softening temperature. For these experiments, the material forming the polymer base matrix of the active substrate was sourced from the Lubrizol Corporation (Ohio, U.S.A.) as follows: (1) PC-3575A, with a vicat softening temperature of 46 degrees Centigrade; PC3585A, with a vicat softening temperature of 58 degrees Centigrade; and PC3572, with a vicat softening temperature of 51 degrees Centigrade.

In both of Experiments 3 and 4 a 200-micron diameter fiberoptic temperature sensor was first inserted inside the tooth with each heating device to measure actual internal temperatures when the heating device was powered up. In each case the inside temperature within the tooth was raised to 80 degrees C. and the outside temperature remained below 55 degrees C. throughout and after applying the heat treatment.

Experiment 3 was performed including placing heating devices within the respective root canals of three teeth pre-inoculated with a *Staphylococcus aureus* biofilm grown into the root of the tooth. An electrical input signal at a power level of 5 W was applied. Once the interior temperature inside the tooth reached 80 degrees C., then the outside temperature of the corresponding tooth was measured. In all three tooth samples for which such measurements were made, there was a time delay before the outside temperature reached 55 C. The duration of the time delay varied, possibly based on the type, size, and shape of the tooth and the root canal. Experiment 3 confirmed that a thermal gradient was created within the tooth.

Experiment 4 was performed similarly to Experiment 3, but in Experiment 4 the substrate material was of durometer A. Disinfection-grade temperatures were achieved within the tooth, and the establishment of a transient thermal cell with corresponding temperature gradients were observed via thermal imaging. The softer durometer A allowed additional softening of the active substrate material, which resulted in better anchoring of the device within the interior of the tooth, which can be useful for sealing purposes, as described herein. In Experiment 4, the heating devices used were un-sintered, such as to help enable greater flexibility and softness.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A dental treatment device comprising:
   a conformal polymer heat-generating substrate, sized and shaped and flexible enough to be inserted into a root canal or a cavity in a tooth to actively generate heat from within the conformal polymer heat-generating substrate, wherein the conformal polymer heat-generating substrate comprises a distal working end portion and includes opposing lateral wings that extend more broadly laterally proximally and less broadly laterally distally to allow folding or rolling into a conical or other tapered structure sized and shaped to be introduced into the root canal or tooth cavity; and a heating transducer included in or carried by the conformal polymer heat-generating substrate into the root canal, the conformal polymer heat-generating substrate configured to actively generate and apply localized heat from within the conformal polymer heat-generating substrate and within root canal or the cavity in the tooth via the conformal polymer heat-generating substrate to treat a target region associated with the tooth.

2. The dental treatment device of claim 1, wherein the heating transducer comprises:

an electrically conductive input structure, to receive an electrically conducted AC electromagnetic signal having a frequency; and a lossy dielectric active substrate region of the conformal polymer heat-generating substrate, coupled to the electrically conductive input structure to receive coupled energy from the electrically conducted AC electromagnetic signal being electrically conducted by the electrically conductive input structure, and to transduce at least some of the coupled energy received into heat to at least one of disrupt biofilm, or sterilize the target region associated with the tooth.

3. The dental treatment device of claim 2, further comprising:

a temperature sensor, sized and shaped to be inserted into the root canal or the cavity in a tooth; and wherein the heating transducer is coupled to controller circuitry to be controlled, based at least in part on temperature information provided by the temperature sensor, to provide enough localized heat at a temperature and duration sufficient to at least one of disrupt biofilm, or sterilize the target region associated with the tooth, while maintaining an external surface of the tooth at or below a specified safety temperature.

4. The dental treatment device of claim 2, wherein the heating transducer includes an AC frequency addressable resonator, responsive to a specified activation frequency of an applied AC electromagnetic input signal.

5. The dental treatment device of claim 4, wherein the heating transducer, which is at least one of included in or carried by the conformal polymer heat-generating substrate into the root canal, includes multiple AC frequency addressable resonators, at least two of which are individually addressable via different specified activation frequencies of the applied AC electromagnetic input signal.

6. The dental treatment device of claim 2, wherein:

the electrically conductive input structure includes multiple layers, the multiple layers including both at least one electrically conductive layer and at least one electrically insulative layer.

7. The dental treatment device of claim 2, wherein:

the conformal polymer heat-generating substrate includes a first region, doped with a first dopant and a second region, doped with a different second dopant.

8. The dental treatment device of claim 7, wherein the first dopant includes carbon and wherein the different second dopant includes barium titanate.

9. The dental treatment device of claim 7, wherein the first region is doped with the first dopant to better absorb coupled electrical energy relative to the second region that is doped with the different second dopant.

10. The dental treatment device of claim 1, where the conformal polymer heat-generating substrate is softenable, in response to heat generated in the conformal polymer heat-generating substrate by the heating transducer, to form a seal in the root canal or the cavity in the tooth.

11. A dental treatment device comprising:

a conformal polymer heat-generating substrate, sized and shaped and flexible enough to be inserted into a root canal or a cavity in a tooth to actively generate heat from within the conformal polymer heat-generating substrate;

a heating transducer included in or carried by the conformal polymer heat-generating substrate into the root canal, the conformal polymer heat-generating substrate configured to actively generate and apply localized heat from within the conformal polymer heat-generating substrate and within root canal or the cavity in the tooth via the conformal polymer heat-generating substrate to treat a target region associated with the tooth; and a thermally insulative plug, shield, or reservoir sized and shaped to be located in association with a proximal root canal opening of the tooth to retain heated fluid or other heat in the root canal or tooth cavity or the reservoir while applying localized heating.

12. The dental treatment device of claim 11, comprising a distal working end portion and includes opposing lateral wings that extend more broadly laterally proximally and less broadly laterally distally to allow folding or rolling into a conical or other tapered structure sized and shaped to be introduced into the root canal or tooth cavity.

* * * * *